United States Patent [19]

Ferrini et al.

[11] 4,451,471
[45] May 29, 1984

[54] CERTAIN 2,4,5-TRI-SUBSTITUTED THIAZOLES, PHARMACEUTICAL COMPOSITIONS CONTAINING SAME AND METHODS OF USING SAME

[75] Inventors: Pier G. Ferrini, Binningen; Richard Göschke, Bottmingen, both of Switzerland

[73] Assignee: Ciba-Geigy Corporation, Ardsley, N.Y.

[21] Appl. No.: 355,989

[22] Filed: Mar. 8, 1982

[30] Foreign Application Priority Data

Mar. 18, 1981 [CH] Switzerland ............... 1838/81

[51] Int. Cl.³ ............... C07D 417/04; A61K 31/44
[52] U.S. Cl. ............... 424/263; 546/270; 546/280
[58] Field of Search ............... 546/280, 270; 424/263

[56] References Cited

U.S. PATENT DOCUMENTS 3,888,870 6/1975 Jackson ............... 548/186
3,933,840 1/1976 Damm et al. ............... 548/229
4,022,607 5/1977 Jackson ............... 71/78

FOREIGN PATENT DOCUMENTS 2146161 2/1973 France.

OTHER PUBLICATIONS

J. Chromatog, 46, 48-65 (1970).

Primary Examiner—Alan L. Rotman
Attorney, Agent, or Firm—Irving N. Feit

[57] ABSTRACT

2,4,5-Trisubstituted thiazoles of the formula

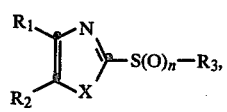

in which each of
$R_1$ and $R_2$, independently of the other, represents an aryl or optionally N-oxidized heteroaryl radical each of which is unsubstituted or substituted by aliphatic hydrocarbon radicals, free, etherified or esterified hydroxy, etherified optionally S-oxidized mercapto, aliphatically substituted amino and/or trifluoromethyl, X represents thio, n represents 0, 1, or 2, and $R_3$ represents an aliphatic hydrocarbon radical that is unsubstituted or substituted by etherified or esterified hydroxy, etherified optionally S-oxidized mercapto and/or, in a position higher than the α-position, by oxo and/or hydroxy and optionally contains, in addition to terminally bonded hydroxy, sulpho that is present in salt form, or represents an araliphatic hydrocarbon radical that is unsubstituted or substituted in the aryl moiety as indicated for $R_1$ and $R_2$, or represents a cycloaliphatic or cycloaliphatic-aliphatic hydrocarbon radical that is unsubstituted or substituted in a position higher than the α-position by free, etherified or esterified hydroxy, or represents a group of the formula

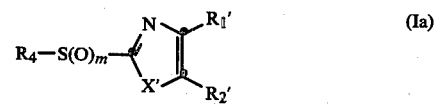

in which m represents, 0, 1 or 2, $R_4$ represents an aliphatic hydrocarbon radical that is unsubstituted or substituted by etherified or esterified hydroxy, optionally S-oxidized etherified mercapto or, in a position higher than the α-position and lower than the ω-position, by oxo and/or hydroxy and that is optionally interrupted by oxa or thia, which may also be S-oxidized, or, if n and m represent O, represents a direct bond, and $R_1'$ and $R_2'$ have one of the meanings given for $R_1$ and $R_2$, and pharmaceutically acceptable salts thereof are suitable for combating rheumatic disorders, preferably as active ingredients in anti-rheumatic medicaments. The invention relates to medicaments of this type and to non-chemical processes for their manufacture, and also to novel compounds of the formula I and to processes for their manufacture.

26 Claims, No Drawings

CERTAIN 2,4,5-TRI-SUBSTITUTED THIAZOLES, PHARMACEUTICAL COMPOSITIONS CONTAINING SAME AND METHODS OF USING SAME

The invention relates to the use of 2,4,5-trisubstituted thiazoles of the formula

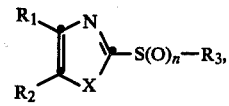

in which each of
$R_1$ and $R_2$, independently of the other, represents an aryl or optionally N-oxidised heteroaryl radical each of which is unsubstituted or substituted by aliphatic hydrocarbon radicals, free, etherified or esterified hydroxy, etherified optionally S-oxidised mercapto, aliphatically substituted amino and/or trifluoromethyl,
X represents thio,
n represents 0, 1 or 2, and
$R_3$ represents an aliphatic hydrocarbon radical that is unsubstituted or substituted by etherified or esterified hydroxy, etherified optionally S-oxidised mercapto and/or, in a position higher than the α-position, by oxo and/or hydroxy and optionally contains, in addition to terminally bonded hydroxy, sulpho that is present in salt form, or represents an araliphatic hydrocarbon radical that is unsubstituted or substituted in the aryl moiety as indicated for $R_1$ and $R_2$, or represents a cycloaliphatic or cycloaliphatic-aliphatic hydrocarbon radical that is unsubstituted or substituted in a position higher than the α-position by free, etherified or esterified hydroxy, or represents a group of the formula

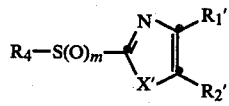

in which m represents 0, 1 or 2, $R_4$ represents an aliphatic hydrocarbon radical that is unsubstituted or substituted by etherified or esterified hydroxy, optionally S-oxidised etherified mercapto or, in a position higher than the α-position and lower than the ω-position, by oxo and/or hydroxy and that is optionally interrupted by oxa or thia, which may also be S-oxidised, or, if n and m represent 0, represents a direct bond, and $R_1'$ and $R_2'$ have one of the meanings given for $R_1$ and $R_2$,
and to pharmaceutically acceptable salts thereof, for combating rheumatic disorders, preferably as active ingredient in anti-rheumatic medicaments, and to medicaments of this type, and to non-chemical processes for their manufacture.

The invention relates also to compounds of the formula I in which $R_1$, $R_2$, X, n, $R_3$, $R_4$, m and $R_2'$ have the meanings given above, with the proviso that, in compounds in which n represents 1, if $R_3$ represents alkyl, at least one of the radicals $R_1$ and $R_2$ is other than phenyl that is unsubstituted or substituted by alkyl, alkoxy, halogen and/or trifluoromethyl, and pharmaceutically acceptable salts thereof, for use in a method for the therapeutic treatment of the human or animal body, to their use for combating diseases, especially as active ingredient in or for the manufacture of pharmaceutical compositions, to pharmaceutical compositions that contain these compounds, and to non-chemical processes for their manufacture.

The invention relates equally to compounds of the formula I in which $R_1$, $R_2$, X, n, $R_3$, $R_4$, m, $R_1'$ and $R_2'$ have the meanings given above, themselves, with the proviso that, in compounds in which n represents 0, if $R_3$ represents alkyl, at least one of the radicals $R_1$ and $R_2$ is other than phenyl that is unsubstituted or substituted by alkyl, alkoxy, halogen and/or trifluoromethyl, and with the further proviso that, in compounds in which n represents 0, if $R_3$ represents ω-hydroxy- or ω-oxo-lower alkyl having more than 3 carbon atoms, at least one of the radicals $R_1$ and $R_2$ represents a heteroaryl radical that is unsubstituted or substituted as indicated or, if $R_3$ represents ω-hydroxy- or ω-oxo-lower alkyl having 2 or 3 carbon atoms, at least one of the radicals $R_1$ and $R_2$ represents a heteroaryl radical that is unsubstituted or substituted as indicated or each of the radicals $R_1$ and $R_2$ represents p-methoxyphenyl, and salts thereof, and to processes for their manufacture.

Aliphatic hydrocarbon radicals are monovalent or, in the case of $R_4$ radicals, divalent. Monovalent aliphatic hydrocarbon radicals are, for example, lower alkyl radicals and, in the case of $R_3$, also lower alkenyl or lower alkynyl radicals. Divalent aliphatic hydrocarbon radicals are, for example, lower alkylene or lower alkenylene radicals.

Etherified hydroxy is, for example, hydroxy etherified by an aliphatic alcohol, such as lower alkoxy, lower alkenyloxy, lower alkynyloxy or, in the case of two etherified hydroxy groups bonded to an aliphatic radical or to vicinal carbon atoms of an aryl or heteroaryl radical, lower alkylenedioxy.

Esterified hydroxy is, for example, hydroxy esterified by a hydrohalic acid or an organic carboxylic acid, such as halogen, lower alkanoyloxy, or benzoyloxy or pyridoyloxy each of which may be substituted as indicated for $R_1$ and $R_2$, for example by lower alkyl, lower alkoxy and/or halogen.

Etherified mercapto is, for example, aliphatically etherified mercapto, such as lower alkylthio or, in the case of two etherified mercapto groups bonded to an aliphatic radical or to vicinal carbon atoms of an aryl or heteroaryl radical, lower alkylenedithio. S-oxidised etherified mercapto is, for example, lower alkanesulphinyl or lower alkanesulphonyl.

Aliphatically substituted amino is, for example, amino substituted by lower alkyl or lower alkylene or aza-, oxa- or thia-lower alkylene, such as mono- or di-lower alkylamino or 4- to 7-membered lower alkyleneamino or 3-aza-, 3-oxa- or 3-thia-lower alkyleneamino.

Aryl radicals are, for example, aryl radicals having from 6 up to and including 10 carbon atoms (C-atoms) as ring members, especially phenyl and also naphthyl.

Optionally N-oxidised heteroaryl radicals are, for example, monocyclic 5-membered heteroaryl radicals having an oxygen or sulphur atom and optionally, in addition, a nitrogen atom, or monocyclic optionally N-oxidised 6-membered heteroaryl radicals having one or two nitrogen atom(s), such as furyl, for example 2-furyl, thienyl, for example 2-thienyl, thiazolyl, for example 2-thiazolyl, optionally N-oxidised pyridyl, for example 2-, 3- or 4-pyridyl, or 3- or 4-(1-oxido)-pyridyl, or pyrimidyl, such as 2-pyrimidyl.

Aliphatic hydrocarbon radicals that are unsubstituted or substituted by etherified or esterified hydroxy, etherified optionally S-oxidised mercapto and/or, in a position higher than the α-position, by oxo and/or hydroxy are, in the case of $R_3$, monovalent hydrocarbon radicals optionally substituted as indicated and, in the case of $R_4$, divalent hydrocarbon radicals optionally substituted as indicated and optionally interrupted by oxa or optionally S-oxidised thia. Monovalent aliphatic hydrocarbon radicals are, for example, lower alkyl, lower alkenyl or lower alkynyl radicals. As divalent aliphatic hydrocarbon radicals optionally interrupted by oxa or optionally S-oxidised thia there come into consideration, for example, lower alkylene, oxa-lower alkylene or optionally S-oxidised thia-lower alkylene. Examples of radicals $R_3$ of this type that may be mentioned are: lower alkyl, lower alkenyl or lower alkynyl, mono- or di-lower alkoxy-lower alkyl, lower alkylenedioxy-lower alkyl, lower alkylidenedioxy-lower alkyl, mono- or di-lower alkanoyloxy-lower alkyl carrying the lower alkanoyloxy* group(s) in a position higher than the α-position, poly-halo-lower alkyl, mono- or di-lower alkylthio-lower alkyl, lower alkanesulphinyl- or lower alkanesulphonyl-lower alkyl, lower alkylenedithio-lower alkyl, or any one of the following, each of which carries the hydroxy group(s) or the lower alk(anoyl)oxy group in a position higher than the α-position: mono- or di-hydroxy-lower alkyl, hydroxy-lower alkoxy-lower alkyl and lower alkanoyloxy-lower alkoxy-lower alkyl, ω-hydroxy-ω-sulpho-lower alkyl, ω-hydroxy-ω-sulpho-lower alkenyl and ω-hydroxy-ω-sulpho-lower alkynyl, each present in salt form, and also lower alkoxy-lower alkoxy-lower alkyl, lower alkylthio-lower alkoxy-lower alkyl, hydroxy-lower alkylthio-lower alkyl, lower alkoxy-lower alkylthio-lower alkyl or lower alkanoyloxy-lower alkylthio-lower alkyl, or oxo-lower alkyl carrying the oxo group in a position higher than the α-position. As radicals $R_4$ of the type described above there come into consideration, for example: lower alkylene, lower alkenylene bonded via a saturated carbon atom, lower alkoxy-lower alkylene, mono- or di-lower alkanoyloxy-lower alkylene carrying the lower alkanoyloxy group in a position higher than the α-position and lower than the ω-position, polyhalo-lower alkylene, lower alkylthio-lower alkylene, and mono- or di-hydroxy- or oxo-lower alkylene carrying the hydroxy or oxo group in a position higher than the α-position and lower than the ω-position, and also oxo-lower alkylene, and optionally S-oxidised thia-lower alkylene.

*Translator's note: Although only "alkanoyl" appears in the German text, it has been assumed that "alkanoyloxy" was intended.

Araliphatic hydrocarbon radicals optionally substituted in the aryl moiety as indicated for $R_1$ and $R_2$ are, for example, phenyl-lower alkyl radicals that are unsubstituted or substituted as indicated, especially by lower alkyl, lower alkoxy, halogen and/or trifluoromethyl.

Cycloaliphatic and cycloaliphatic-aliphatic hydrocarbon radicals optionally substituted in a position higher than the α-position by free, etherified or esterified hydroxy are, for example, cycloalkyl and cycloalkyl-lower alkyl radicals, or hydroxycycloalkyl, lower alkoxycycloalkyl or lower alkanoyloxycycloalkyl or cycloalkyl-(hydroxy)-lower alkyl, each carrying the hydroxy, lower alkoxy or lower alkanoyloxy group in a position higher than the α-position and each having from 3 to 8, preferably from 5 to 7, ring members.

Hereinbefore and hereinafter, organic radicals and compounds that are termed "lower" are preferably to be understood as meaning those containing up to and including 7, especially up to and including 4, carbon atoms (C atoms).

Lower alkyl is, for example, methyl, ethyl, propyl, isopropyl, butyl, isobutyl, sec.-butyl or tert.-butyl, also pentyl, hexyl or heptyl.

Lower alkenyl is, for example, vinyl, but preferably lower alkenyl bonded via a saturated carbon atom, such as allyl, methallyl or but-2-enyl.

Lower alkynyl is, for example, ethynyl, but preferably lower alkynyl bonded via a saturated carbon atom, such as propargyl or but-2-ynyl.

Lower alkoxy is, for example, methoxy, ethoxy, propoxy, isopropoxy, butoxy, isobutoxy, sec.-butoxy, or tert.-butoxy, also pentyloxy, hexyloxy or heptyloxy.

Lower alkenyloxy is, for example, allyloxy, and lower alkynyloxy is, for example, propargyloxy.

Lower alkylenedioxy is, for example, geminally bonded ethylenedioxy, 1,3-propylenedioxy, 2,3-butylenedioxy or 1,3-(2,2-dimethyl)-propylenedioxy.

Lower alkylidenedioxy is, for example, vicinally bonded methylenedioxy, ethylidenedioxy or isopropylidenedioxy.

Lower alkanoyloxy is, for example acetoxy, propionyloxy, butyryloxy, isobutyryloxy, also formyloxy or pivaloyloxy.

Lower alkylthio is, for example, methylthio, ethylthio, propylthio, isopropylthio, butylthio, isobutylthio, sec.-butylthio or tert.-butylthio, also pentylthio, hexylthio or heptylthio.

Lower alkylenedithio is, for example, geminally bonded ethylenedithio, 1,3-propylenedithio or 1,3-(2,2-dimethyl)-propylenedithio.

Lower alkylidenedithio is, for example, vicinally bonded methylenedithio, ethylidenedithio or isopropylidenedithio.

Lower alkanesulphinyl is, for example, methane-, ethane-, 1- or 2propane-, butane- or isobutane-sulphinyl.

Lower alkanesulphonyl is, for example, methane-, ethane-, 1- or 2-propane-, butane- or isobutane-sulphonyl.

Mono- or di-lower alkylamino is, for example, methylamino, dimethylamino, ethylamino, diethylamino, propylamino or butylamino.

4- to 7-membered lower alkyleneamino or 3-aza-, 3-oxa- or 3-thia-lower alkyleneamino is, for example, pyrrolidin-1-yl, piperidino, morpholino, thiomorpholino or piperazin-1-yl or 4-methyl- or 4-ethyl-piperazin-1-yl.

Lower alkylene is, for example, ethylene, 1,3-propylene, 1,4-butylene or 1,3-(2,2-dimethyl)-propylene, also 1,5-pentylene, 1,6-hexylene or 1,7-heptylene.

Oxa-lower alkylene is, for example, 1,5-(3-oxa)-pentylene, 1,6-(3-oxa)-hexylene or 1,7-(4-oxa)-heptylene, also 1,4-(2-oxa)-butylene or 1,5-(2-oxa)-pentylene.

Optionally S-oxidised thia-lower alkylene is, for example, optionally S-mono- or S,S-di-oxidised 1,5-(3-thia)-pentylene, 1,6-(3-thia)-hexylene or 1,7-(4-thia)-heptylene, also optionally S-mono- or S,S-di-oxidised 1,4-(2-thia)-butylene or 1,5-(2-thia)-pentylene.

Mono- or di-lower alkoxy-lower alkyl is, for example, 2-methoxy-, 2-ethoxy-, 2-propoxy- or 2-isopropoxy-ethyl, 3-methoxy- or 3-ethoxy-propyl, or 3,3-dimethoxy-, 3,3-diethoxy-, 2,3-dimethoxy- or 2,3-diethoxy-propyl, or 4,4-dimethoxybutyl, also methoxy-, ethoxy-, dimethoxy- or propoxy- or isopropoxy-methyl.

Lower alkylenedioxy-lower alkyl is, for example, 2,2-ethylenedioxy- or 2,2-propylenedioxy-ethyl, or 3,3- or 2,3-ethylenedioxy-propyl, also ethylenedioxy- or propylenedioxy-methyl.

Lower alkylidenedioxy-lower alkyl is, for example, 2,3-methylenedioxy-, 2,3-ethylidenedioxy- or 2,3-isopropylidenedioxy-propyl.

Mono- or di-lower alkanoyloxy-lower alkyl carrying the lower alkanoyloxy group(s) in a position higher than the α-position is, for example, 2-acetoxyethyl or 3-acetoxy- or 2,3-diacetoxy-propyl, but may also be 2,3-succinyldioxy-propyl.

Polyhalo-lower alkyl contains as halogen especially fluorine and represents, for example 1,1,2,2-tetrafluoroethyl or 1,1,2,2,2-pentafluoroethyl, also trifluoromethyl.

Mono- or di-lower alkylthio-lower alkyl represents, for example, 2-methylthio-, 2-ethylthio-, 2-propylthio- or 2-isopropylthio-ethyl, 3-methylthio- or 3-ethylthio-propyl, or 3,3-bis(methylthio)-, 3,3-bis(ethylthio)-, 2,3-bis(methylthio)- or 2,3-bis(ethylthio)-propyl, or 4,4-bis(methylthio)-butyl, also methylthio-, ethylthio-, bis(methylthio)-, propylthio- or isopropylthio-methyl.

Lower alkanesulphinyl-lower alkyl is, for example, 2-methanesulphinyl-, 3-ethanesulphinyl-, 2-propanesulphinyl- or 2-(2propanesulphinyl)-ethyl, 3-methanesulphinyl- or 3-ethanesulphinyl-propyl, also methanesulphinyl-, ethanesulphinyl- or 1- or 2-propanesulphinyl-methyl.

Lower alkanesulphonyl-lower alkyl is, for example, 2-methanesulphonyl-, 3-ethanesulphonyl-, 2propanesulphonyl- or 2-(2-propanesulphonyl)-ethyl, 3-methanesulphonyl- or 3-ethanesulphonyl-propyl, also methanesulphonyl-, ethanesulphonyl- or 1- or 2-propanesulphonyl-methyl.

Lower alkylenedithio-lower alkyl is, for example, 2,2-ethylenedithio- or 2,2-propylenedithio-ethyl, or 3,3- or 2,3-ethylenedithio-propyl, also ethylenedithio- or propylenedithio-methyl.

Lower alkylidenedithio-lower alkyl is, for example, 2,3-propylidenedithio-, 2,3-ethylidenedithio- or 2,3-isopropylidenedithio-propyl.

Mono- or di-hydroxy-lower alkyl carrying the hydroxy group(s) in a position higher than the α-position is, for example, 2-hydroxyethyl, 3-hydroxy- or 2,3-dihydroxy-propyl, 4-hydroxy- or 2,4-dihydroxy-butyl, 5-hydroxy-, 2,5-dihydroxy- or 3,5-dihydroxy-pentyl, also 3,4-dihydroxybutyl or 4,5-dihydroxypentyl.

Hydroxy-lower alkoxy-lower alkyl carrying the hydroxy group(s) in a position higher than the α-position represents, for example, 2-(2-hydroxyethoxy)-, 2-(3-hydroxypropoxy)- or 2-(2,3-dihydroxyethoxy)-ethyl or 3-(2-hydroxyethoxy)- or 3-(3-hydroxypropoxy)-propyl, also 2-hydroxyethoxy- or 3-hydroxypropoxy-methyl.

Lower alkanoyloxy-lower alkoxy-lower alkyl carrying the lower alkanoyloxy group in a position higher than the α-position is, for example, 2-(2-acetoxyethoxy)- or 2-(3-acetoxypropoxy)-ethyl, or 3-(2-acetoxyethoxy)-propyl, also 2-acetoxyethoxy- or 3-acetoxypropoxy-methyl. ω-Hydroxy-ω-sulpho-lower alkyl, -lower alkenyl and -lower alkynyl represents, for example, 2-hydroxy-2-sulphoethyl, 3-hydroxy-3-sulpho-propyl, -1-prop-1-enyl or -prop-1-ynyl, or 4-hydroxy-4-sulphobutyl, -but-2-enyl or -but-2-ynyl.

Lower alkoxy-lower alkoxy-lower alkyl represents, for example, 2-(methoxyethoxy)-, 2-(ethoxymethoxy)-, 2-(2-methoxypropoxy)- or 2-(2-ethoxyethoxy)-ethyl, or 3-(2-methoxyethoxy)-propyl, also methoxyethoxy-, ethoxymethoxy- or ethoxyethoxy-methyl.

Hydroxy-lower alkylthio-lower alkyl carrying the hydroxy group(s) in a position higher than the α-position represents, for example, 2-(2-hydroxyethylthio)-, 2-(3-hydroxypropylthio)- or 2-(2,3-dihydroxypropylthio)-ethyl, or 3-(2-hydroxyethylthio)- or 3-(3-hydroxypropylthio)-propyl, also 2-hydroxyethylthio- or 3-hydroxypropylthio-methyl.

Lower alkanoyloxy-lower alkylthio-lower alkyl carrying the lower alkanoyloxy group in a position higher than the α-position represents, for example, 2-(2-acetoxyethylthio)- or 2-(3-acetoxypropylthio)-ethyl, or 3-(2-acetoxyethylthio)-propyl, also 2-acetoxyethylthio- or 3-acetoxypropylthio-methyl.

Oxo-lower alkyl carrying the oxo group in a position higher than the α-position is, for example, 2-oxoethyl, 2- or 3-oxopropyl, or 2-, 3- or 4-oxobutyl, also corresponding oxopentyl, oxohexyl or oxoheptyl.

Lower alkenylene bonded via a saturated carbon atom represents also but-2-enylene, pent-2-enylene, pent-3- enylene or hex-3-enylene.

Mono- or di-hydroxy-lower alkylene carrying the hydroxy group(s) in a position higher than the α-position and lower than the ω-position represents, for example, 1,3-(2-hydroxy)-propylene, 1,4-(2- or 3-hydroxy)- or 1,4-(2,3-dihydroxy)-butylene, or 1,5-(3-hydroxy)- or 1,5-(2,4-dihydroxy)-pentylene.

Lower alkoxy-lower alkylene is, for example, 1,3-(2-methoxy)- or 1,3-(2-ethoxy)-propylene, or 1,4-(2- or 3-methoxy)-butylene, also 2-methoxy- or 2-ethoxy-ethylene.

Mono- or di-lower alkanoyloxy-lower alkylene carrying the lower alkanoyloxy group(s) in a position higher than the α-position and lower than the ω-position represents, for example, 1,3-(acetoxy)-propylene, 1,4-(2- or 3-acetoxy)-butylene or 1,4-(2,3-diacetoxy)-butylene, also 1,5-(3-acetoxy)-pentylene.

Polyhalo-lower alkylene contains as halogen especially fluorine and represents, for example, 1,1,2,2-tetrafluoroethylene.

Lower alkylthio-lower alkylene is, for example, 1,3-(2-methylthio)- or 1,3-(2-ethylthio)-propylene.

Oxo-lower alkylene carrying the oxo group in a position higher than the α-position and lower than the ω-position represents, for example, 1,3-(2-oxo)-propylene, 1,4-(2- or 3-oxo)-butylene or 1,5-(3-oxo)-pentylene.

Phenyl-lower alkyl is, for example, benzyl, 2-phenylethyl or 3-phenylpropyl.

Cycloalkyl having from 3 to 8 ring members is, for example, cyclopentyl, cyclohexyl or cycloheptyl, also cyclopropyl or cyclooctyl.

Cycloalkyl-lower alkyl is, for example, 1-cycloalkyl-lower alkyl, such as cyclopentyl-, cyclohexyl- or cycloheptylmethyl.

Hydroxycycloalkyl carrying the hydroxy group in a position higher than the α-position is, for example, 2-hydroxycycloalkyl, such as 2-hydroxycyclopentyl, 2-hydroxycyclohexyl or 2-hydroxycycloheptyl. Lower alkoxycycloalkyl or lower alkanoyloxycycloalkyl carrying the lower alkoxy or lower alkanoyloxy group in a position higher than the α-position is, for example, 2-methoxy- or 2-ethoxy- or 2-acetoxy-cyclopentyl, 2-methoxy-, or 2-ethoxy- or 2-acetoxy-cyclohexyl, or 2-methoxy- or 2-ethoxy- or 2-acetoxy-cycloheptyl.

Cycloalkyl-(hydroxy)-lower alkyl is, for example, 2-cyclohexyl-, 2-cyclopentyl- or 2-cycloheptyl-2-hydroxyethyl.

Halogen is, for example, halogen having an atomic number up to and including 35, such as fluorine, chlorine or bromine.

Salts of compounds of the formula I are especially pharmaceutically acceptable acid addition salts with strong acids, such as a mineral acid, for example salts with hydrohalic acids, especially hydrochloric or hydrobromic acid, that is to say, hydrohalides, especially hydrochlorides and hydrobromides, or sulphuric acid salts, that is to say, bisulphates and sulphates, also salts with suitable organic acids, such as dicarboxylic acids or organic sulphonic acids, for example maleates, fumarates, malates, tartrates or methanesulphonates, also N-cyclohexylsulphamates. As further pharmaceutically acceptable salts there come into consideration metal salts, such as alkali metal salts, of compounds of the formula I containing ω-hydroxy-ω-sulpho-lower alkyl, -lower alkenyl and -lower alkynyl $R_4$, especially the potassium salts thereof.

The compounds of the formula I exhibit valuable pharmacological properties. In particular, they exhibit a pronounced anti-nociceptive activity and an inhibitory action on the synthesis of prostaglandin, and also a pronounced anti-inflammatory action. For example, they prove to have excellent action in mice in the phenyl-p-benzoquinone-induced Writhing Syndrome according to J. Pharmacol. exp. Therap. 125, 237, (1959), in a dosage range of approximately 4 to 40 mg/kg p.o.

In doses of approximately 1 to 10 mg/kg p.o. they likewise exhibit a marked inhibitory action on experimental carrageenin paw oedema in rats. They also inhibit in vivo the synthesis of leucotriene $B_4$.

Furthermore, in vitro in a concentration range of approximately 0.1 to 1.0 μm/l, they exhibit a marked inhibitory action on the synthesis of prostaglandin from arachidonic acid, demonstrated in the experimental procedure according to Prostaglandin, 7, 123, (1974).

Accordingly, the compounds of the formula I are especially suitable as active ingredients in pharmaceutical compositions for the treatment of painful inflammatory disorders, especially chronic disorders of the rheumatic type, such as chronic arthritis.

The invention relates especially to the use of compounds of the formula I in which each of $R_1$ and $R_2$, independently of the other, represents aryl having from 6 up to and including 10 carbon atoms, monocyclic 5-membered heteroaryl having an oxygen atom or sulphur atom and optionally, in addition, a nitrogen atom, or monocyclic optionally N-oxidised 6-membered heteroaryl having one or two nitrogen atom(s), each of which is unsubstituted or substituted by lower alkyl, lower alkoxy or, at vicinal carbon atoms, by lower alkylidenedioxy, by hydroxy, halogen or lower alkanoyloxy, or by benzoyloxy or pyridoyloxy each of which is unsubstituted or substituted by lower alkyl, lower alkoxy and/or by halogen, by lower alkylthio or, at vicinal carbon atoms, by lower alkylidenedithio, by lower alkanesulphinyl, lower alkanesulphonyl, amino, mono- or di-lower alkylamino, 3- to 7-membered alkylene- or 3-aza-, 3-oxa- or 3-thia-lower alkylene-amino, nitro and/or by trifluoromethyl, X represents thio, n represents 0, 1 or 2, $R_3$ represents lower alkyl, or lower alkenyl or lower alkynyl each of which is preferably bonded via a saturated carbon atom, mono- or di-lower alkoxy-lower alkyl, lower alkylenedioxy-lower alkyl, lower alkylidenedioxy-lower alkyl, mono- or di-lower alkanoyloxy-lower alkyl carrying the lower alkanoyloxy group(s) in a position higher than the α-position, polyhalo-lower alkyl, mono- or di-lower alkylthio-lower alkyl, lower alkanesulphinyl- or lower alkanesulphonyl-lower alkyl, lower alkylenedithio-lower alkyl, or any one of the following, each of which carries the hydroxy group(s) or the lower alk(anoyl)oxy group in a position higher than the α-position: mono- or di-hydroxy-lower alkyl, hydroxy-lower alkoxy-lower alkyl or lower alkanoyloxy-lower alkoxy-lower alkyl, ω-hydroxy-ω-sulpho-lower alkyl, ω-hydroxy-ω-sulpho-lower alkenyl and ω-hydroxy-ω-sulpho-lower alkynyl, each present in salt form, and lower alkoxy-lower alkoxy-lower alkyl, lower alkylthio-lower alkoxy-lower alkyl, hydroxy-lower alkylthio-lower alkyl, lower alkoxy-lower alkylthio-lower alkyl or lower alkanoyloxy-lower alkylthio-lower alkyl, or oxo-lower alkyl carrying the oxo group in a position higher than the α-position, or phenyl-lower alkyl that is unsubstituted or substituted as indicated for $R_1$ and $R_2$, 3- to 8-membered cycloalkyl or cycloalkyl-lower alkyl, or hydroxycycloalkyl, lower alkoxycycloalkyl, lower alkanoyloxy-lower alkyl or cycloalkyl-(hydroxy)-lower alkyl, each carrying the hydroxy or lower alk(anoyl)oxy group in a position higher than the α-position, or represents a radical of the formula Ia in which m represents 0, 1 or 2, $R_4$ represents lower alkylene, lower alkenylene bonded via a saturated carbon atom, lower alkoxy-lower alkylene, mono- or di-lower alkanoyloxy-lower alkylene carrying the lower alkanoyloxy group in a position higher than the α-position and lower than the ω-position, polyhalo-lower alkylene, lower alkylthio-lower alkylene, or mono- or di-hydroxy- or oxo-lower alkylene, each carrying the hydroxy or oxo group in a position higher than the α-position and lower than the ω-position, oxa-lower alkylene or optionally S-oxidised thia-lower alkylene, or, if n and m represent 0, represents a direct bond, and $R_1'$ and $R_2'$ have one of the meanings given for $R_1$ and $R_2$ respectively, and to pharmaceutically acceptable salts thereof, for combating rheumatic disorders, preferably as active ingredient in anti-rheumatic medicaments, and to medicaments of this type and to non-chemical processes for their manufacture, and also be compounds of the formula I in which $R_1$, $R_2$, $R_3$, X, n, m, $R_3$, $R_4$, $R_1'$ and $R_2'$ have the meanings given above, with the proviso that, in compounds in which n represents 1, if $R_3$ represents lower alkyl, at least one of the radicals $R_1$ and $R_2$ is other than phenyl that is unsubstituted or substituted by lower alkyl, lower alkoxy, halogen and/or trifluoromethyl, and pharmaceutically acceptable salts thereof, for use in a method for the therapeutic treatment of the human or animal body, to their use for combating diseases, especially as active ingredient in or for the manufacture of pharmaceutical compositions, to pharmaceutical compositions containing these compounds, and to non-chemical processes for their manufacture, and equally to compounds of the formula I in which $R_1$, $R_2$, X, n, $R_3$, $R_4$, m, $R_1'$ and $R_2'$ have the meanings given above, themselves, with the proviso that, in compounds in which n represents 0 or 1, if $R_3$ represents lower alkyl, at least one of the radicals $R_1$ and $R_2$ is other than phenyl that is unsubstituted or substituted by lower alkyl, lower alkoxy, halogen and/or trifluoromethyl, and with the further proviso that, in compounds in which n represents 0, if $R_3$ represents ω-hydroxy- or ω-oxo-lower alkyl having more than 3 carbon atoms, at least one of the radicals $R_1$ and $R_2$ represents heteroaryl according to the above definition that is unsubstituted or substituted as indicated, or, if $R_3$ represents ω-hydroxy- or ω-oxo-lower alkyl having 2 or 3 carbon atoms, at least one of the radicals $R_1$ and $R_2$ represents heteroaryl according to the above definition or each of the radicals $R_1$ and $R_2$ represents p-methoxyphenyl, to salts, especially pharmaceutically acceptable salts, thereof and to processes for their manufacture.

The invention relates especially to the use of compounds of the formula I in which each of $R_1$ and $R_2$, independently of the other, represents phenyl that is unsubstituted or substituted by lower alkyl, lower alkoxy, hydroxy, halogen, lower alkanoyloxy, lower alkylthio, lower alkanesulphonyl, di-lower alkylamino, 3- to 7-membered alkylene- or 3-aza-, 3-oxa- or 3-thia-lower alkylene-amino and/or trifluoromethyl, or furyl, such as 2-furyl, thienyl, pyridyl, such as 2-, 3- or 4-pyridyl, or 1-oxidopyridyl, such as 2-, 3- or 4-(1-oxido)-pyridyl, each of which is unsubstituted or substituted by lower alkyl, lower alkoxy or hydroxy, X represents thio, n represents 0, 1 or 2, $R_3$ represents lower alkyl, of lower alkenyl or lower alkynyl each of which is bonded via a saturated carbon atom, mono- or di-lower alkoxy-lower alkyl, lower alkylenedioxy-lower alkyl, lower alkylidenedioxy-lower alkyl, mono- or di-lower alkanoyloxy-lower alkyl carrying the lower alkanoyloxy group(s) in a position higher than the α-position, or mono- or di-lower alkylthio-lower alkyl, or any one of the following, each of which carries the hydroxy group(s), the lower alk(anoyl)oxy group or the lower alkylenedioxy group in a position higher than the α-position: mono- or di-hydroxy-lower alkyl, hydroxy-lower alkoxy-lower alkyl or lower alkanoyloxy-lower alkoxy-lower alkyl, lower alkoxy-lower alkoxy-lower alkyl, lower alkylthio-lower alkoxy-lower alkyl, hydroxy-lower alkylthio-lower alkyl, lower alkoxy-lower alkylthio-lower alkyl or lower alkanoyloxy-lower alkylthio-lower alkyl, ω-hydroxy-ω-sulpho-lower alkyl, ω-hydroxy-ω-sulpho-lower alkenyl and ω-hydroxy-ω-sulpho-lower alkynyl, each present in salt form, and/or oxo-lower alkyl carrying the oxo group in a position higher than the α-position, or represents a radical of the formula Ia in which m represents 0, 1 or 2, $R_4$ represents lower alkylene, or hydroxy-lower alkylene, lower alkanoyloxy-lower alkylene or oxo-lower alkylene, each carrying the hydroxy, lower alkanoyloxy or oxo group in a position higher than the α-position and lower than the ω-position, or, if n and m represent 0, represents a direct bond, and $R_1'$ and $R_2'$ have one of the meanings given for $R_1$ and $R_2$, and pharmaceutically acceptable salts thereof, for combating rheumatic disorders, preferably as active ingredient in anti-rheumatic medicaments, and to medicaments of this type and to non-chemical processes for their manufacture, and also to compounds of the formula I in which $R_1$, $R_2$, X, n, $R_3$, $R_4$, m, $R_1'$ and $R_2'$ have the meanings given above, with the proviso that, in compounds in which n represents 1, if $R_3$ represents lower alkyl, at least one of the radicals $R_1$ and $R_2$ is other than phenyl that is unsubstituted or substituted by lower alkyl, lower alkoxy, halogen and/or trifluoromethyl, and pharmaceutically acceptable salts thereof, for use in a method for the therapeutic treatment of the human or animal body, to their use for combating diseases, especially as active ingredient in or for the manufacture of pharmaceutical compositions, to pharmaceutical compositions that contain these compounds and to non-chemical processes for their manufacture, and equally to compounds of the formula I in which $R_1$, $R_2$, X, n, $R_3$, $R_4$, X', m, $R_1'$ and $R_2'$ have the meanings given above, themselves, with the proviso that, in compounds in which n represents 0 or 1, if $R_3$ represents lower alkyl, at least one of the radicals $R_1$ and $R_2$ is other than phenyl that is unsubstituted or substituted by lower alkyl, lower alkoxy, halogen and/or trifluoromethyl, and with the further proviso that, in compounds in which n represents 0, if $R_3$ represents ω-hydroxy- or ω-oxo-lower alkyl having more than 3 carbon atoms, at least one of the radicals $R_1$ and $R_2$ represents furyl, thienyl, pyridyl or 1-oxidopyridyl, each of which is unsubstituted or substituted as indicated, or if $R_3$ represents ω-hydroxy- or ω-oxo-lower alkyl having 2 or 3 carbon atoms, at least one of the radicals $R_1$ and $R_2$ represents furyl, thienyl, pyridyl or 1-oxidopyridyl, each of which is unsubstituted or substituted as indicated, or each of the radicals $R_1$ and $R_2$ represents p-methoxyphenyl, and salts, especially pharmaceutically acceptable salts, thereof, and to processes for their manufacture.

The invention relates specifically to the use of compounds of the formula I in which each of $R_1$ and $R_2$, independently of the other, represents phenyl that is unsubstituted or substituted by lower alkoxy, halogen, lower alkylthio, lower alkanesulphinyl, di-lower alkylamino and/or trifluoromethyl, or unsubstituted thienyl, such as 2-thienyl, or unsubstituted or hydroxy-substituted optionally N-oxidised pyridyl, such as 3- or 4-pyridyl, or 3- or 4-(1-oxido)-pyridyl, X represents thio, n represents 0, 1 or 2, $R_3$ represents lower alkyl, or lower alkenyl or lower alkynyl each of which is bonded via a saturated carbon atom, lower alkoxy-lower alkyl, lower alkanoyloxy-lower alkyl carrying the lower alkanoyloxy group in a position higher than the α-position, lower alkylthio-lower alkyl, or any one of the following, each of which carries the hydroxy group or the lower alk(anoyl)oxy group in a position higher than the α-position: hydroxy-lower alkyl, hydroxy-lower alkoxy-lower alkyl or lower alkanoyloxy-lower alkoxy-lower alkyl, ω-hydroxy-ω-sulpho-lower alkyl that is present in salt form, lower alkoxy-lower alkoxy-lower alkyl, lower alkylthio-lower alkoxy-lower alkyl, or oxo-lower alkyl carrying the oxo group in a position higher than the α-position, and pharmaceutically acceptable salts thereof, for combating rheumatic disorders, preferably as active ingredient in anti-rheumatic medicaments, and to medicaments of this type and to non-chemical processes for their manufacture, and also to compounds of the formula I in which $R_1$, $R_2$, X, n, $R_3$, $R_4$, X', m, $R_1'$ and $R_2'$ have the above meanings, with the proviso that in compounds in which n represents 1, if $R_3$ represents lower alkyl, at least one of the radicals $R_1$ and $R_2$ is other than phenyl that is unsubstituted or substituted by lower alkyl, lower alkoxy, halogen and/or trifluoromethyl, and pharmaceutically acceptable salts thereof, for use in a process for the therapeutic treatment of the human or animal body, to their use for combating diseases, especially as active ingredient in or for the manufacture of pharmaceutical compositions, to pharmaceutical compositions containing these compounds and to non-chemical processes for their manufacture, and equally to compounds of the formula I in which $R_1$, $R_2$, X, n, $R_3$, $R_4$, m, X', $R_1'$ and $R_2'$ have the meanings given above, themselves, with the proviso that, in compounds in which n represents 0 or 1, if $R_3$ represents lower alkyl, at least one of the radicals $R_1$ and $R_2$ is other than phenyl that is unsubstituted or substituted by lower alkyl, lower alkoxy, halogen and/or trifluoromethyl, and with the further proviso that, in compounds in which n represents 0, if $R_3$ represents ω-hydroxy- or ω-oxo-lower alkyl having more than 3 carbon atoms, each of $R_1$ and $R_2$ represents thienyl or pyridyl, or if $R_3$ represents ω-hydroxy- or ω-oxo-lower alkyl having 2 or 3 carbon atoms, $R_1$ and/or $R_2$ is thienyl or pyridyl or each of $R_1$ and $R_2$ represents p-methoxyphenyl, and salts thereof, and to processes for their manufacture.

The invention relates more especially, on the one hand, to compounds of the formula I in which at least one of the radicals $R_1$ and $R_2$ represents optionally N-oxidised pyridyl, such as 3- or 4-pyridyl or 3- or 4-(1-oxido)-pyridyl, or thienyl, such as 2-thienyl, and the other represents phenyl that is unsubstituted or substituted by lower alkoxy having up to and including 4 carbon atoms, such as methoxy, lower alkylthio having up to and including 4 carbon atoms, such as methylthio, halogen having an atomic number of up to and including 35, such as fluorine or chlorine, hydroxy and/or trifluoromethyl, X represents thio, n represents 0, 1 or 2, and in which $R_3$ represents either lower alkyl having up to and including 4 carbon atoms, such as ethyl, polyhalo-lower alkyl in which halogen has an atomic number of up to and including 35 and lower alkyl has up to and including 4 carbon atoms, such as trifluoromethyl or 1,1,2,2-tetrafluoroethyl, or any one of the following, each of which carries the hydroxy, lower alkanoyloxy, lower alkoxy, lower alkylthio, lower alkanesulphinyl or lower alkanesulphonyl group in a position higher than the α-position: hydroxy-lower alkyl having from 2 up to and including 7 carbon atoms, such as 2-hydroxyethyl, lower alkanoyloxy-lower alkyl, each moiety having up to and including 4 carbon atoms, such as 2-acetoxyethyl, lower alkoxy-lower alkyl, each moiety having up to and including 4 carbon atoms, such as 2-methoxyethyl, or lower alkylthio-, lower alkanesulphinyl- or lower alkanesulphonyl-lower alkyl*, each moiety having up to and including 4 carbon atoms, such as 2-methylthio-, 2-methanesulphinyl- or 2-methanesulphonylethyl, or hydroxy-lower alkoxy-lower alkyl, such as 2-(2-hydroxyethoxy)-ethyl, or hydroxy-lower alkylthio-lower alkyl, such as 2-(2-hydroxyethylthio)-ethyl, each carrying the hydroxy group and the hydroxy-lower alkoxy or hydroxy-lower alkylthio group in a position higher than the α-position, or $R_3$ represents lower alkyl having up to and including 4 carbon atoms, such as ethyl, or any one of the following, each of which carries the oxo, hydroxy, lower alkanoyloxy, lower alkoxy or lower alkylenedioxy group(s) in a position higher than the α-position: oxo- or hydroxy-lower alkyl each having up to and including 4 carbon atoms, such as 2-hydroxyethyl, 3-hydroxypropyl, 2-oxoethyl or 3-oxopropyl, lower alkanoyloxy-lower alkyl, each moiety having up to and including 4 carbon atoms, such as 2-acetoxyethyl, mono- or di-lower alkoxy-lower alkyl, each moiety having up to and including 4 carbon atoms, such as 2,2-dimethoxyethyl or 3,3-dimethoxypropyl, or lower alkylenedioxy-lower alkyl, each moiety having up to and including 4 carbon atoms, such as 2,2-ethylenedioxyethyl, or ω-hydroxy-ω-sulpho-lower alkyl that is present in salt form and has from 2 to 4 carbon atoms, such as 2-hydroxy-2-sulphoethyl, and salts, especially pharmaceutically acceptable salts, thereof, to processes for their manufacture, to pharmaceutical compositions that contain these compounds or the pharmaceutically acceptable salts thereof, and to their use.

*Translator's note: Although "-lower alkyl" does not appear in the German text, it has been assumed this was omitted in error.

The invention relates especially, on the other hand, to compounds of the formula I in which each of $R_1$ and $R_2$, independently of the other, represents phenyl that is unsubstituted or substituted by lower alkoxy having up to and including 4 carbon atoms, such as methoxy, lower alkylthio having up to and including 4 carbon atoms, such as methylthio, halogen having an atomic number of up to and including 35, such as fluorine or chlorine, hydroxy and/or trifluoromethyl, X represents thio, n represents 0 or 2, and in which $R_3$ represents either lower alkyl having up to and including 4 carbon atoms, such as ethyl, polyhalo-lower alkyl in which halogen has an atomic number of up to and including 35 and lower alkyl has up to and including 4 carbon atoms, such as trifluoromethyl or 1,1,2,2-tetrafluoroethyl, or represents any one of the following, each of which carries the hydroxy, lower alkanoyloxy, lower alkoxy, lower alkylthio, lower alkanesulphinyl or lower alkanesulphonyl group in a position higher than the α-position: hydroxy-lower alkyl having from 2 up to and including 7 carbon atoms, such as 2-hydroxyethyl, lower alkanoyloxy-lower alkyl, each moiety having up to and including 4 carbon atoms, such as 2-acetoxyethyl, lower alkoxy-lower alkyl, each moiety having up to and including 4 carbon atoms, such as 2-methoxyethyl, or lower-alkylthio-, lower alkanesulphinyl- or lower alkanesulphonyl-lower alkyl,* each moiety having up to and including 4 carbon atoms, such as 2-methylthio-, 2-methanesulphinyl- or 2-methanesulphonylethyl, or hydroxy-lower alkoxy-lower alkyl, such as 2-(2-hydroxyethyl)-ethyl, or hydroxy-lower alkylthio-lower alkyl, such as 2-(2-hydroxyethylthio)-ethyl, each carrying the hydroxy group and the hydroxy-lower alkoxy or hydroxy-lower alkylthio group in a position higher than the α-position, or $R_3$ represents lower alkyl having up to and including 4 carbon atoms, such as ethyl, or any one of the following, each of which carries the oxo, hydroxy, lower alkanoyloxy, lower alkoxy or lower alkylenedioxy group(s) in a position higher than the α-position: hydroxy-lower alkyl having from 2 up to and including 4 carbon atoms, such as 2-hydroxyethyl or 3-hydroxypropyl, lower alkanoyloxy-lower alkyl, each moiety having up to and including 4 carbon atoms, such as 2-acetoxyethyl, oxo-lower alkyl having up to and including 4 carbon atoms, such as 2-oxoethyl or 3-oxopropyl, or mono- or di-lower alkoxy-lower alkyl or lower alkylenedioxy-lower alkyl, each having up to and including 4 carbon atoms in each alkyl(ene) moiety, such as 2-methoxyethyl, 2,2-dimethoxyethyl, 3,3-dimethoxypropyl or 2,2-ethylenedioxyethyl, or ω-hydroxy-ω-sulpho-lower alkyl that is present in salt form and has from 2 to 4 carbon atoms, such as 2-hydroxy-2-sulphoethyl, and pharmaceutically acceptable salts thereof, for use in a method for the treatment of the human or animal body, especially for use as active ingredient in or for the manufacture of pharmaceutical compositions, and to such compositions, and also to compounds of the formula I in which $R_1$, $R_2$ and X have the meanings given above, n represents 0, 1 or 2, and in which $R_3$ represents either polyhalo-lower alkyl in which halogen has an atomic number of up to and including 35 and lower alkyl has up to and including 4 carbon atoms, such as trifluoromethyl or 1,1,2,2-tetrafluoroethyl, or any one of the following, each of which carries the lower alkanoyloxy, lower alkoxy, lower alkylthio, lower alkanesulphinyl or lower alkanesulphonyl group in a position higher than the α-position: lower alkanoyloxy-lower alkyl, each moiety having up to and including 4 carbon atoms, such as 2-acetoxyethyl, lower alkoxy-lower alkyl, each moiety having up to and including 4 carbon atoms, such as 2-methoxyethyl, or lower alkylthio-, lower alkanesulphinyl- or lower alkanesulphonyl-lower alkyl*, each moiety having up to and including 4 carbon atoms, such as 2-methylthio-, 2-methanesulphinyl- or 2-methanesulphonyl-ethyl, or hydroxy-lower alkoxy-lower alkyl, such as 2-(hydroxyethoxy)-ethyl, or hydroxy-lower alkylthio-lower alkyl, such as 2-(2-hydroxyethylthio)-ethyl, each carrying the hydroxy group and the hydroxy-lower alkoxy** or hydroxy-lower alkylthio group in a position higher than the α-position, or hydroxy-lower alkyl having from 2 up to and including 4 carbon atoms and carrying the hydroxy group in a position higher than the α-position and lower than the ω-position, such as 2-hydroxypropyl, or, if n represents 2, lower alkyl having from 2 up to and including 7 carbon atoms, such as ethyl, or, if n represents 1 or 2, ω-hydroxy-lower alkyl having from 2 up to and including 7 carbon atoms, such as 2-hydroxyethyl, or $R_3$ represents any one of the following, each of which carries the lower alkanoyloxy, lower alkoxy or lower alkylenedioxy group(s) in a position higher than the α-position: lower alkanoyloxy-lower alkyl, each moiety having up to and including 4 carbon atoms, such as 2-acetoxyethyl, mono- or di-lower alkoxy-lower alkyl or lower alkylenedioxy-lower alkyl, each moiety having up to and including 4 carbon atoms, such as 2-methoxyethyl, 2,2-dimethoxyethyl, 3,3-dimethoxypropyl or 2,2-ethylenedioxyethyl, or ω-hydroxy-ω-sulpho-lower alkyl that is present in salt form and has from 2 to 4 carbon atoms, such as 2-hydroxy-2-sulphoethyl, or, if n represents 2, lower alkyl having from 2 up to and including 7 carbon atoms, such as ethyl, or, if n represents 1 or 2, ω-hydroxy-lower alkyl or ω-oxo-lower alkyl having from 2 up to and including 4 carbon atoms, such as 2-hydroxyethyl or 2-oxoethyl, or, if n represents 0 and each of the radicals $R_1$ and $R_2$ represents p-methoxyphenyl, ω-hydroxy- or ω-oxo-lower alkyl having 2 or 3 carbon atoms, such as 2-hydroxyethyl, 3-hydroxypropyl, 2-oxoethyl or 3-oxopropyl, and salts, especially pharmaceutically acceptable salts, thereof, and to processes for their manufacture.

*See note on page 20.
**Translator's note: Although "alkyl" appears in the German text, it has been assumed that "alkoxy" was intended.

The invention relates more especially, on the one hand, to compounds of the formula I in which at least one of the radicals $R_1$ and $R_2$ represents pyridyl, for example 3- or 4-pyridyl, or thienyl, for example 2-thienyl, and the other represents phenyl that is unsubstituted or substituted, preferably in the p-position, by lower alkoxy having up to and including 4 carbon atoms, such as methoxy, or halogen having an atomic number of up to and including 35, such as fluorine or chlorine, X represents thio or oxy, n represents 0, 1 or 2, and in which $R_3$ represents either lower alkyl having up to and including 4 carbon atoms, such as ethyl, ω-hydroxy-lower alkyl having from 2 to 4 carbon atoms, such as 2-hydroxyethyl, 2- or 3-lower alkoxy-lower alkyl or 2- or 3-lower alkylthio-lower alkyl having up to and including 4 carbon atoms, such as 2-methoxyethyl or 2-methylthioethyl, or 2- or 3-(ω-hydroxy-lower alkoxy)- or 2- or 3-(ω-hydroxy-lower alkylthio)-lower alkyl having up to and including 4 carbon atoms, such as 2-(2-hydroxyethoxy)-ethyl or 2-(2-hydroxyethylthio)-ethyl, or $R_3$ represents lower alkyl having up to and including 4 carbon atoms, such as ethyl, ω-hydroxy-ω-sulpho-lower alkyl that is present in salt form and has from 2 to 4 carbon atoms, such as 2-hydroxy-2-sulphoethyl, ω-hydroxy-lower alkyl having from 2 to 4 carbon atoms, such as 2-hydroxyethyl, ω,ω-di-lower alkoxy-lower alkyl having up to and including 4 carbon atoms, such as 2,2-dimethoxyethyl or 3,3-dimethoxypropyl, ω-lower alkanoyloxy-lower alkyl, each moiety having up to and including 4 carbon atoms, such as 2-acetoxyethyl, or ω-oxo-lower alkyl having up to and including 4 carbon atoms, such as 2-oxoethyl or 3-oxopropyl, and salts, especially pharmaceutically acceptable salts, thereof, to processes for their manufacture, to pharmaceutical compositions containing these compounds or their pharmaceutically acceptable salts, and to their use.

The invention relates more especially, on the other hand, to compounds of the formula I in which each of $R_1$ and $R_2$, independently of the other, represents phenyl that is unsubstituted or substituted, especially in the p-position, by lower alkoxy having up to and including 4 carbon atoms, such as methoxy, or halogen having an atomic number of up to and including 35, such as fluorine or chlorine, X represents thio, n represents 0, 1 or 2, and in which $R_3$ represents either ω-hydroxy-lower alkyl having from 2 to 4 carbon atoms, such as 2-hydroxyethyl, 2- or 3-lower alkoxy-lower alkyl or 2- or 3-lower alkylthio-lower alkyl having up to and including 4 carbon atoms, such as 2-methoxyethyl or 2-methylthioethyl, or 2- or 3-(ω-hydroxy-lower alkoxy)- or 2- or 3-(ω-hydroxy-lower alkylthio)-lower alkyl having up to and including 4 carbon atoms, such as 2-(2-hydroxyethoxy)-ethyl or 2-(2-hydroxyethylthio)-ethyl, or if n represents 0 or 2, lower alkyl having up to and including 4 carbon atoms, such as ethyl, or ω,ω-di-lower alkoxy-lower alkyl, having up to and including 4 carbon atoms in each alkyl moiety, such as 2,2-dimethoxyethyl or 2,2-dimethoxy-propyl, or ω-lower alkanoyloxy-lower alkyl, each moiety having up to and including 4 carbon atoms, such as 2-acetoxyphenyl, or, if n represents 0 or 2, lower alkyl having up to and including 4 carbon atoms, such as ethyl, and pharmaceutically acceptable salts thereof, for use in a method for the therapeutic treatment of the human or animal body, especially to their use as active ingredient in or for the manufacture of pharmaceutical compositions, and to such pharmaceutical compositions, and also to compounds of the formula I in which $R_1$, $R_2$, X and n have the meanings given above, and in which $R_3$ represents either 2- or 3-lower alkoxy-lower alkyl or 2- or 3-lower alkylthio-lower alkyl having up to and including 4 carbon atoms, such as 2-methoxyethyl or 2-methylthioethyl, or 2- or 3-(ω-hydroxy-lower alkoxy)- or 2- or 3-(ω-hydroxy-lower alkylthio)-lower alkyl having up to and including 4 carbon atoms, such as 2-(2-hydroxyethyl)-ethyl or 2-(2-hydroxyethylthio)-ethyl, or if n represents 2, lower alkyl having up to and including 4 carbon atoms, such as ethyl, or, if n represents 1 or 2, ω-hydroxy-lower alkyl having from 2 up to and including 4 carbon atoms, such as 2-hydroxyethyl, or $R_3$ represents ω-hydroxy-ω-sulpho-lower alkyl that is present in salt form and has from 2 to 4 carbon atoms, such as 2-hydroxy-2-sulphoethyl, ω-di-lower alkoxy-lower alkyl or ω-lower alkanoyloxy-lower alkyl, each moiety having up to and including 4 carbon atoms, such as 2,2-dimethoxyethyl or 2-acetoxyethyl, or ω-lower alkylenedioxy-lower alkyl, each moiety having up to and including 4 carbon atoms, such as 2,2-ethylenedioxyethyl, or, if n represents 2, lower alkyl having up to and including 4 carbon atoms, such as ethyl, or, if n represents 1 or 2, ω-hydroxy-lower alkyl or ω-oxo-lower alkyl having from 2 up to and including 4 carbon atoms, such as 2-hydroxyethyl or 2-oxoethyl, or, if n represents 0 and each of $R_1$ and $R_2$ represents p-methoxyphenyl, ω-hydroxy- or ω-oxo-lower alkyl having 2 or 3 carbon atoms, such as 2-hydroxyethyl or 2-oxoethyl, and salts, especially pharmaceutically acceptable salts, thereof, and to processes for their manufacture.

The invention relates especially to the specific novel compounds of the formula I mentioned in the Examples and to pharmaceutically acceptable salts thereof, to processes for their manufacture, to pharmaceutical compositions that contain them, and to their use.

The compounds of the formula I can be manufactured according to methods known per se, for example, by removing HY from a compound of the formula

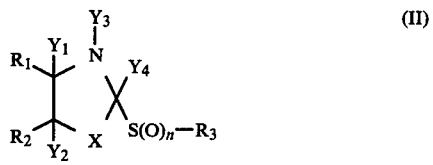

in which one of the radicals $Y_1$ and $Y_2$ represents a removable radical Y and the other represents a hydrogen atom and $Y_3$ and $Y_4$ together represent an additional bond, or in which $Y_4$ represents a removable radical Y, $Y_3$ represents hydrogen and $Y_1$ and $Y_2$ represent an additional bond, or from a salt thereof, with the introduction of an additional bond, if necessary separating a mixture of isomers obtainable according to the process into the pure isomers and, if desired, converting a compound obtainable according to the process into a different compound of the formula I and/or converting a free compound obtainable according to the process into a salt or a salt obtainable according to the process into the free compound.

Removable radicals Y are, for example, optionally esterified or etherified hydroxy or mercapto groups, also amino, ammonio and sulphonium groups. As esterified hydroxy there comes into consideration, for example, hydroxy esterified by an inorganic acid or by an organic carboxylic acid, such as halogen, for example chlorine or bromine, or lower alkanoyloxy, for example acetoxy. Etherified hydroxy groups are, for example, lower alkoxy groups, for example methoxy or ethoxy. Esterified mercapto groups are, for example, mercapto groups esterified by a lower alkanecarboxylic acid, such as acetylthio. Etherified mercapto groups or sulphonium groups are, for example, lower alkylthio or di-lower alkylsulphonium groups, such as methylthio, ethylthio or dimethylsulphonium. Amino groups are, for example, di-lower alkyl- or alylene- or aza-, oxa- or thia-lower alkylene-amino groups, for example dimethylamino, diethylamino, pyrrolidin-1-yl, piperidino, morpholino, thio-morpholino, and also anilino. Ammonium groups are, for example, tertiary ammonium groups corresponding to the above-mentioned amino groups or quaternary ammonium groups, such as tri-lower alkylammonio or pyridinio.

HY is removed usually spontaneously or by heating gently, for example at approximately 40° to 100° C., if necessary in the presence of a condensation agent and-/or an inert solvent. As condensation agents there come into consideration preferably acidic condensation agents when using as starting material compounds of the formula II in which Y represents hydroxy or mercapto or sulphonium, each of which is optionally etherified or esterified by an organic carboxylic acid, or an amino or ammonium group. Such condensation agents are, for example, mineral acids or anhydrides or acidic salts thereof, for example hydrohalic acids, especially hydrochloric, hydrobromic or hydriodic acid, sulphuric acid, alkali metal bisulphates, phosphoric acid, polyphosphoric acid, phosphorus pentoxide or, for the manufacture of compounds of the formula I in which X represents thio, phosphorus pentasulphide, phosphorus trichloride, phosphorus oxychloride or phosphorus tribromide, organic sulphonic acids, such as p-toluenesulphonic acid, or carboxylic acids or anhydrides thereof, such as lower alkanoic acids and anhydrides or halides thereof, for example acetic acid, acetic anhydride or acetyl chloride, and also phosgene.

When using as starting material compounds of the formula II in which Y represents hydroxy esterified by a hydrohalic acid, it is preferable to use basic condensation agents, such as hydroxides, carbonates or lower alkoxides of alkali or alkaline earth metals, for example sodium, potassium or calcium hydroxide, sodium or potassium carbonate or sodium methoxide, and also organic nitrogen bases, such as tri-lower alkylamines, for example triethylamine, or aromatic tertiary bases, such as pyridine.

The starting materials of the formula II can be manufactured according to methods known per se.

Thus, compounds of the formula II in which $Y_1$ represents free, etherified or reactive esterified hydroxy, etherified mercapto or optionally substituted amino, $Y_2$ represents hydrogen, n represents 0 and $Y_3$ and $Y_4$ represent an additional bond, are obtained, for example, by reacting a compound of the formula $R_1$—C(=O)—CH($R_2$)—XH (III), or a functional oxo derivative thereof, with a compound of the formula N≡C—SR$_3$ (IV). Functional oxo derivatives of compounds of the formula III are, for example, ketals thereof, such as di-lower alkyl ketals, thioketals, such as di-lower alkylthioketals, thioxo derivatives, imine derivatives, such as imines or aniles, enamines, such as N,N-di-lower alkyl- or N,N-alkylene- or N,N-oxa- or N,N-thia-alkylene-enamines, or enol ethers, such as enol-lower alkyl ethers. The reaction, in which there is formed intermediately a compound of the formula $R_1$—C(=O)—C(R$_2$)—X—C(=NH)—SR$_3$ (V), or a functional oxo derivative thereof, is effected preferably in an inert solvent, if necessary in the presence of a condensation agent, while cooling or heating and/or under an inert gas atmosphere. As condensation agents there come into consideration, for example, acidic condensation agents, such as mineral acids, for example hydrochloric acid, sulphuric acid, phosphoric acid and the like, and acidic salts thereof, for example sodium bisulphate, phosphorus pentoxide, polyphosphoric acid, phosphorus oxychloride, phosphorus tribromide or tri-lower alkyl phosphites, and also carboxylic acid anhydrides, such as acetyl chloride or acetic anhydride, and organic sulphonic acids, for example p-toluenesulphonic acid. Acidic condensation agents enable the entire reaction sequence (III+IV→V→II→I) to be carried out in a "one pot reaction" without isolation of intermediates, for example of the formulae V and II. The fundamental compounds of the formula III are, where not known, obtainable by condensation of compounds of the formulae $R_1$—C(=O)—Cl (VI) and $R_2$—H (VII) in the presence of aluminium chloride, bromination of the product of the formula $R_1-C(=O)-CH_2-R_2$ (VIII), for example with bromine in acetic acid, reaction with sodium thioacetate and hydrolysis of the product of the formula $R_1-C(=O)-CH(R_2)-X-C(=O)-CH_3$ (IX) and, if desired, functional modification of the oxo group.

In analogous manner it is also possible to react an aminoketone of the formula $R_1-CH(NH_2)-C(=O)-R_2$ (X), or a functional oxo derivative thereof, such as a ketal, thioketal, geminal dihalide or thioxo derivative, with a compound of the formula Hal-$C(=X')-S-R_3$ (XI) in which Hal represents halogen and $X'$ represents thioxo, or to react it first with a reactive carbonic acid or thiocarbonic acid derivative, such as a diester, ester halide or dihalide of thiocarbonic acid or trithiocarbonic acid, for example with a thiocarbonic acid lower alkyl ester, a thiocarbonic acid ester halide or thiophosgene, and then with a mercaptan of the formula $R_3-Y_6$ (XII, $Y_6$=mercapto) to form a compound of the formula $R_1-CH[NH-C(=X')-SR_3]-C(=O)-R_2$ (XIII), or a functional oxo derivative thereof, which cyclises spontaneously or by heating gently, if necessary in the presence of a condensation agent, to form a compound of the formula II in which $Y_1$ represents hydrogen, $Y_2$ represents optionally etherified hydroxy or mercapto, or halogen, and $Y_3$ together with $Y_4$ represents an additional bond, or $Y_1$ together with $Y_2$ represents an additional bond, $Y_3$ represents hydrogen and $Y_4$ represents hydroxy or mercapto. As condensation agents there come into consideration, when using as starting material compounds of the formula XIII themselves and functional thioxo derivatives thereof, and when using as starting material geminal di-halo derivatives of compounds of the formula XIII, for example, basic condensation agents, and when using as starting material ketals or thioketals derived from compounds of the formula XIII either acidic or basic condensation agents. Acidic condensation agents are, for example, those mentioned and as basic condensation agents there come into consideration, for example, metal bases, such as hydroxides, carbonates or lower alkoxides of alkali metals or alkaline earth metals, for example sodium, potassium or calcium hydroxide, sodium or potassium carbonate or sodium methoxide, and also tertiary or quaternary nitrogen bases, such as tri-lower alkylamines, for example triethylamine, or heteroaromatic bases, for example pyridine. It is also possible, however, to use as starting materials compounds of the formula XIII in which $X'$ represents oxo and to treat these with phosphorus pentasulphite. It is possible, especially in the presence of an acidic condensation agent, also to carry out the aforementioned reactions in a "one pot reaction", without isolation of intermediates (for example of the formulae XIII and II). The aminoketones of the formula X serving as starting materials can be manufactured, for example, by reacting a compound of the formula $R_1-CH-C(=O)-R_2$ (XIV) with hydroxylamine to form an oxime, esterifying this with p-toluenesulphochloride and treating the resulting oxime ester with an alkali metal alkoxide, for example with potassium tert.-butoxide.

Another procedure consists in reacting a compound of the formula $R_1-C(=O)-CH(Z)-R_2$ (XVII) with a compound of the formula $X=C(NH_2)-SR_3$ (XV) in which $X'$ represents thioxo, Z in the formula XVII representing reactive esterified hydroxy, such as halogen or sulphonyloxy, for example methane-, ethane-, ethene-, benzene-, p-bromobenzene- or, especially, p-toluene-sulphonyloxy, and also fluorosulphonyloxy. By this procedure there is obtained likewise with the primary formation of an intermediate, for example of the formula V ($X$=thio) or XIII ($X'$=oxo), and cyclisation, a compound of the formula II in which one of the radicals $Y_1$ and $Y_2$ represents hydroxy and the other represents hydrogen and $Y_3$ and $Y_4$ represent an additional bond.

The reaction of a compound of the formula XVII with a compound of the formula XV is preferably carried out in the presence of a basic or acidic condensation agent, it being possible in the case of the former to halt at the stage of the intermediate of the formula II and to isolate this. Basic or acidic condensation agents are preferably those mentioned. Instead of using an acidic condensation agent it is also possible, however, to use the component of the formula XV in the form of an acid addition salt.

The compounds of the formula I can also be manufactured by condensing with one another compounds of the formulae

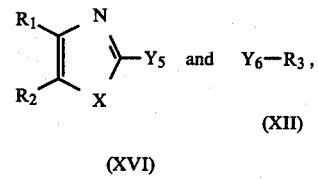

in which $Y_5$ represents a group of the formula $-S(O)_n-H$ or $-S-SH$, which is optionally present in salt form, and $Y_6$ represents reactive esterified hydroxy or, if $R_3$ has at least one additional C—C bond in the α,β-position, etherified hydroxy, or $Y_5$ represents reactive esterified hydroxy, and $Y_6$ represents a group of the formula $-SH-$ or $-S-SH$, which is optionally present in salt form, and if necessary, separating a mixture of isomers obtainable according to the process into the pure isomers and, if desired, converting a compound obtainable according to the process into a different compound of the formula I and/or converting a free compound obtainable according to the process into a salt or a salt obtainable according to the process into the free compound.

Reactive esterified hydroxy groups are, for example, hydroxy groups esterified by mineral acids or organic sulphonic acids, such as halogen, for example chlorine, bromine or iodine, lower alkanesulphonyl, for example methane- or ethane-sulphonyl, or optionally substituted benzenesulphonyl, for example benzene-, p-toluene- or p-bromobenzene-sulphonyl, and also fluorosulphonyl. Etherified hydroxy $Y_6$ is, for example, lower alkoxy, such as isopropoxy or, especially, tert.-butoxy.

As salt forms of the group $-S(O)_n-H$ or $-S-SH$ there come into consideration, for example, metal salt forms thereof, such as alkali metal or alkaline earth metal salt forms, and in the case of groups $-S(O)_n-H$ in which n represents 1 or 2, also the ammonium salt forms thereof with ammonia or organic amines. Salts of this type are preferably produced in situ by the action of an equivalent amount of the relevant base on the reactant containing the free group $-S(O)_n-H$ or by reaction of a compound of the formula XVI or XII in which $Y_5$ or $Y_6$, respectively, represents halogen, with sodium disulphide, and used without isolation.

Condensation is effected in customary manner, preferably in an inert solvent, if necessary while cooling or heating, for example in a temperature range of approximately 0° to 100° C., in a closed vessel and/or under an inert gas atmosphere, such as a nitrogen atmosphere. As inert solvents there come into consideration especially polar solvents, such as lower alkanols, di-lower alkyl ketones, N,N-di-lower alkyl alkanecarboxylic acid amides or N-lower alkyl lactams or di-lower alkyl sulphoxides, if $Y_6$ represents etherified hydroxy in the presence of dilithium palladium tetrachloride.

The starting materials of the formula XVI can be manufactured according to methods known per se.

For example, compounds of the formula XVI in which $Y_5$ represents halogen or organic sulphonyloxy are manufactured, for example, by reacting a compound of the formula $R_1-C(=O)-CH(Z)-R_2$ (XVII) in which Z represents reactive esterified hydroxy, for example halogen, with an inorganic isothiocyanate, preferably in ethanol, and treating the condensation product of the formula $R_1-C(=O)-CH[X-(C\equiv N)-]-R_2$ (XIX) with a hydrohalic acid or organic sulphonic acid, preferably in benzene or diethyl ether.

Compounds of the formula XVI in which $Y_5$ represents a group $-S(O)_n-H$ and n represents 0 can be obtained, for example, by reacting a compound of the formula XVII with ammonium dithiocarbamate, or reacting a corresponding compound of the formula XVI in which $Y_5$ represents halogen with thiourea or sodium thioacetate and freeing the desired mercaptan therefrom by solvolysis or reduction.

Compounds of the formula XVI in which $Y_5$ represents a group $-S(O)_n-H$ and n represents 0 are obtained also by reacting a compound of the formula $R_1-C(=O)-CH(R_2)-XH$ (III) with ammonium thiocyanate or an alkali metal thiocyanate, preferably while heating in ethanolic hydrochloric acid.

Compounds of the formula XVI in which $Y_5$ represents a group $-S(O)_n-H$ and n represents 1 or 2 can be manufactured, for example, by oxidation of the corresponding compounds in which n represents 0. As oxidising agents there come into consideration, for the manufacture of sulphinic acids ($Y_5=SO_2-H$), for example hydrogen peroxide in the presence of an acid and, for the manufacture of sulphonic acids ($Y_5=SO_3-H$), for example potassium permanganate and also nitrogen dioxide.

The compounds of the formula I may also be manufactured by condensing with one another compounds of the formulae

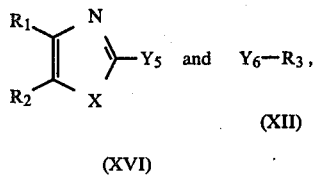 and $Y_6-R_3$, (XVI) (XII)

in which one of the radicals $Y_5$ and $Y_6$ represents a metallic radical and the other represents a group $-S(O)_n-Y_7$ in which $Y_7$ represents reactive esterified hydroxy or, if n represents 1 or 2, etherified hydroxy or, if n represents 0, etherified mercapto, and in which $R_3$ represents or contains an aliphatic hydrocarbon radical that is unsubstituted or substituted by etherified hydroxy and/or mercapto groups and is optionally interrupted by oxa or thia, or an araliphatic* hydrocarbon radical that is unsubstituted or optionally substituted in the aryl moiety as indicated for $R_1$ and $R_2$, or a cycloaliphatic or cycloaliphatic-aliphatic hydrocarbon radical that is unsubstituted or substituted by etherified hydroxy, and, if desired, converting a compound obtainable according to the process into a different compound of the formula I and/or converting a free compound obtainable according to the process into a salt or a salt obtainable according to the process into the free compound.

*Translator's note: Although "aliphatic" appears in the German text, it has been assumed "araliphatic" was intended.

Metallic radicals are, for example, groups of the formulae $-M^I$, $-M^{II}/2$ or $-M^{II}$-Hal in which $M^I$ represents a metal atom of group 1A and $M^{II}$ represents a metal atom of the groups 2A and 2B, of the Periodic Table of Elements and Hal represents a halogen atom, such as chlorine, bromine or iodine.

Reactive esterified hydroxy is, for example, halogen, such as chlorine, bromine or iodine. Etherified hydroxy or mercapto is, for example, lower alkoxy or lower alkylthio, lower alkylidenedioxy or lower alkylidenedithio, or lower alkylenedioxy or lower alkylenedithio, but may also be phenoxy or phenylthio optionally substituted by lower alkyl and/or lower alkoxy. As etherified mercapto groups there come into consideration also groups $Y_5$ of the formula

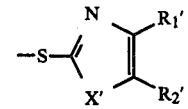

or groups $Y_5$ of the formula $-S-R_3$, in which $R_1'$ and $R_2'$ have one of the meanings indicated for $R_1$ and $R_2$.

The reaction is effected in the customary manner, preferably in an inert solvent, if necessary while cooling or heating and/or under an inert gas atmosphere, for example a nitrogen atmosphere. As inert solvents there come into consideration, for example, ethers, such as di-lower alkyl ethers, for example diethyl ether or tert.-butoxymethane, or lower alkylene ethers, for example tetrahydrofuran, or tertiary amides, for example hexamethylphosphoric acid triamide, and also hydrocarbons, such as benzene. The reaction is carried out, for example, in a temperature range of $-80°$ to approximately $+60°$ C., preferably of approximately $-25°$ to approximately $+40°$ C. In a preferred embodiment of this process, for example a compound of the formula XVI in which $Y_5$ represents a halosulphenyl or halosulphonyl group is used as starting material and this is reacted with a compound of the formula XII in which $Y_6$ represents an alkali metal atom at approximately $-10°$ to $+10°$ C. in tetrahydrofuran or hexamethylphosphoric acid triamide. In another preferred embodiment, for example a compound of the formula XVI in which $Y_5$ represents an alkali metal atom is reacted with a compound of the formula $R_3-S-S-R_3$ (XIIa).

Starting materials of the formula XVI in which $Y_5$ represents a group $-S(O)_n-Y_7$ and $Y_7$ represents halogen are obtained, for example, by halogenating a compound of the formula XVI in which $Y_5$ represents a group $-S(O)_n-H$ in customary manner, when using mercaptans (n=0) as starting material, for example by reaction with chlorine, for example in tetrachloromethane, optionally after prior oxidation to form the disulphide, and when using sulphinic or sulphonic acids (n=1 or 2, respectively) as starting material, by dry heating of the sodium salt with phosphorus pentachloride. From the sulphinyl and sulphonyl chlorides obtainable in this manner the corresponding esters (Y$_5$=etherified hydroxy) are obtained by reaction with an alcohol or alcoholate, for example with a lower alkanol or alkali metal lower alkoxide.

Compounds of the formula XVI in which Y$_5$ represents a metallic radical can be manufactured, for example, by reacting a compound of the formula

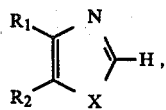

(XVIII)

which can be obtained, for example, by reacting a compound of the formula R$_1$—C(=O)—CH(Z)—R$_2$ (XVII, Z=reactive esterified hydroxy, for example halogen) with thioformamide, with an organometal compound, such as an alkali metal or alkaline earth metal hydrocarbon compound, for example with butyllithium, phenylsodium or butylmagnesium bromide. It is also possible, however, to use a compound of the formula XVI in which Y$_5$ represents halogen as starting material and to react this with an alkali or alkaline earth metal, for example with magnesium or lithium.

Disulphides of the formula

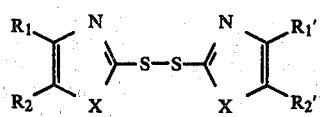

(XVIa)

or of the formula R$_3$—S—S—R$_3$ (XIIa) are obtained, for example, by oxidation of the corresponding mercaptans of the formula XVI and XII, respectively, (Y$_5$ or Y$_6$=—S(O)$_n$—H, n=0), for example by means of air or by treatment with iodine.

A further process for the manufacture of compounds of the formula I is characterised in that a compound of the formula

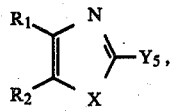

(XVI)

in which Y$_5$ represents mercapto, or a salt thereof, is reacted with a vicinal epoxy derivative derived from a compound of the formula R$_3$—H (XIX) to form a compound of the formula I in which R$_3$ has a hydroxy group in the β-position and n represents 0, and, if necessary, a mixture of isomers obtainable according to the process is separated into the pure isomers and, if desired, a compound obtainable according to the process is converted into a different compound of the formula I and/or a free compound obtainable according to the process is converted into a salt or a salt obtainable according to the process is converted into the free compound.

As salts of compounds of the formula XVI there come into consideration, for example, metal salts thereof, preferably alkali metal or alkaline earth metal salts.

Vicinal epoxides derived from compounds of the formula XIX are, for example, vicinal aliphatic, araliphatic, cycloaliphatic or cycloaliphatic-aliphatic epoxides that are unsubstituted or substituted as indicated for R$_3$, such as 1,2-epoxy-lower alkanes, 1,2-epoxycycloalkanes or cycloalkyl-1,2-epoxy-lower-alkanes.

The reaction is effected in the customary manner, for example in an inert solvent, such as a lower alkanol, or a tertiary amide, for example in hexamethylphosphoric acid triamide, if necessary in the presence of a condensation agent, for example, when using free mercaptans of the formula XVI as starting material, in the presence of a basic agent that is capable of forming salts, such as an alkali metal alcoholate or hydroxide, for example sodium methoxide or sodium hydroxide, while cooling or heating and/or under an inert gas atmosphere, such as a nitrogen atmosphere.

A further process for the manufacture of compounds of the formula I is characterised in that a compound of the formula

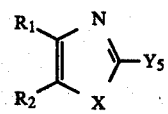

(XVI)

in which Y$_5$ represents mercapto, or a salt thereof, is reacted with a compound of the formula R$_3$'-H (XX) in which R$_3$' represents a radical that is derived from R$_3$ and has at least one C—C double bond or C—C triple bond to form a compound of the formula I in which R$_3$ is α,β-saturated or α,β-singly unsaturated and n represents 0 and, if necessary, a mixture of isomers obtainable according to the process is separated into the pure isomers and, if desired, a compound obtainable according to the process is converted into a different compound of the formula I and/or a free compound obtainable according to the process is converted into a salt or a salt obtainable according to the process is converted into the free compound.

As salts of mercaptans of the formula XVI there come into consideration especially metal salts thereof, preferably alkali metal or alkaline earth metal salts.

Radicals R$_3$' having at least one C—C double bond or C—C triple bond are, for example, aliphatic hydrocarbon radicals having at least one C—C double bond or C—C triple bond, araliphatic hydrocarbon radicals having at least one non-aromatic C—C double bond or one C—C triple bond, cycloaliphatic hydrocarbon radicals having at least one C—C double bond or cycloaliphatic-aliphatic* hydrocarbon radicals having at least one C—C double bond or C—C triple bond in the aliphatic moiety, the hydrocarbon radicals in each case being unsubstituted or substituted as indicated for R$_3$, or are radicals that are derived from radicals of the formula Ia and have at least one non-aromatic C—C double bond or one C—C triple bond. As compounds of the formula XX there come into consideration, for example: lower alkenes, lower alkanedienes, lower alkynes, lower alkynenes, or any of the following, each of which carries the lower alkoxy, lower alkylenedioxy, lower alkylidenedioxy, lower alkylthio, lower alkanesulphenyl, lower alkanesulphonyl, hydroxy, hydroxy-lower alkoxy, lower alkanoyloxy-lower alkoxy, lower alkoxy-lower alkoxy, lower alkylthio-lower alkoxy, hydroxy-lower alkylthio, lower alkoxy-lower alkylthio, lower alkanoyloxy-lower alkylthio or oxo group(s) in a position higher than the β-position: mono- or di-lower alkoxy-lower alkenes, lower alkylenedioxy-lower alkenes, lower alkylidenedioxy-lower alkenes, di-lower alkanoyloxy-lower alkenes, polyhalo-lower alkenes, mono- or di-lower alkylthio-lower alkenes, lower alkanesulphinyl- or lower alkanesulphonyl-lower alkenes, lower alkylenedithio-lower alkenes, mono- or di-hydroxy-lower alkenes, hydroxy-lower alkoxy-lower alkenes, lower alkanoyloxy-lower alkoxy-lower alkenes, lower alkoxy-lower alkoxy-lower alkenes, lower alkylthio-lower alkoxy-lower alkenes, hydroxy-lower alkylthio-lower alkenes, lower alkoxy-lower alkylthio-lower alkenes, lower alkanoyloxy-lower alkylthio-lower alkenes and oxo-lower alkenes, or phenyl-lower alkenes or -lower alkynes substituted in the phenyl moiety as indicated for R₃, cycloalkenes and cycloalkyl-lower alkenes or alkynes, and also compounds of the formula

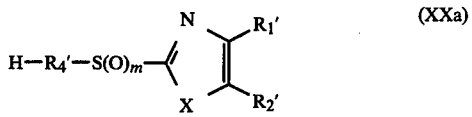

that contain as the radical R₄' lower alkenylene, lower alkadienylene, 3-lower alkoxy-lower alk-1-enylene, 3-lower alkanoyloxy-lower alk-1-enylene, polyhalo-lower alkenylene, 3-lower alkylthio-lower alk-1-enylene or mono- or di-hydroxy- or oxo-lower alkenylene, each carrying the hydroxy or oxo group in a position higher than the β-position and lower than the ω-position, also 4-oxa-lower alk-1-enylene or optionally S-oxidised 4-thia-lower alk-1-enylene.

*Translator's note: Although here only "cycloaliphatic" appears in the German text, it has been assumed that "cycloaliphatic-aliphatic" was intended.

The reaction is effected in the customary manner, for example in an inert solvent, such as a tertiary amide, for example in dimethylformamide or N-methylpyrrolidone, if necessary in the presence of a condensation agent, while cooling or heating and/or under an inert gas atmosphere, for example a nitrogen atmosphere. As condensation agents there come into consideration, when using mercaptans of the formula XVI as starting material, for example organic nitrogen bases, such as di- or tri-lower alkylamines, for example diisopropylamine or triethylamine, or alkylene- or aza-, oxa- or thia-alkylene-amines, for example pyrrolidine, piperidine, morpholine, thiomorpholine or piperazine.

Compounds of the formula I in which R₃ represents a group of the formula Ia, n and m represent 0 and R₄ represents a direct bond, can also be manufactured by condensing with one another compounds of the formulae

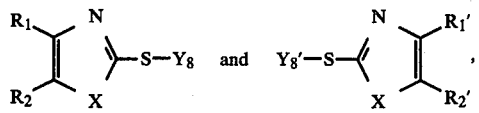

(XXI)          (XXII)

in which the radicals Y₈ and Y₈' are groups that can be removed with the formation of a bond, and, if necessary, separating a mixture of isomers obtainable according to the process into the pure isomers and, if desired, converting a compound obtainable according to the process into a different compound of the formula I and/or converting a free compound obtainable according to the process into a salt or a salt obtainable according to the process into the free compound.

Groups Y₈ and Y₈' that can be removed with the formation of a bond are, for example, hydrogen atoms. Further pairs Y₈ and Y₈' that can be removed with the formation of a bond are, for example, mercapto, which may optionally be present in salt form, for example in alkali metal salt form, and halogen, for example chlorine, and sulphonic acid groups of the formula —SO₃H that are present in salt form, for example in alkali metal salt form. The variants in which Y₈ and Y₈' are identical and represent, for example, hydrogen or sulphonic acid groups that are present in salt form, are especially suitable for the manufacture of symmetric disulphides (R₁=R₁', R₂'=R₂), whilst the reaction of compounds of the formulae XXI and XXII in which Y₈ and Y₈' are different and Y₈ (Y₈') represents, for example, mercapto that is present in salt form and Y₈' (Y₈) represents, for example, halogen, may also be used for the manufacture of asymmetic disulphides.

Y₈ and Y₈' are removed, with the formation of a bond, in customary manner, when using as starting materials compounds in which Y₈ and Y₈' represent hydrogen or sulphonic acid groups that are present in salt form, for example by the action of a suitable oxidising agent, advantageously in an inert solvent, if necessary while cooling or heating and/or under an inert gas atmosphere, such as a nitrogen atmosphere. Suitable oxidising agents are, for example, halogens, such as bromine or, especially, iodine, preferably in an acetic acid, alcoholic and/or aqueous solution, alkali metal hypohalites, for example sodium hypoiodide, which is preferably produced in situ, for example by introducing iodine into aqueous and/or alcoholic sodium hydroxide solution, and, for the oxidative removal of hydrogen, also hydrogen peroxide, for example in approximately 10% strength aqueous solution, or iron trichloride in ether.

The starting materials of the formulae XXI and XXII can be manufactured according to methods known per se, Bunte salts (Y₈=Y₈'=sulphonic acid groups present in salt form) being manufactured, for example, by reacting the corresponding compounds of the formula

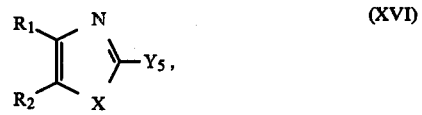

in which Y₅ represents halogen with a salt of thiosulphuric acid, for example sodium thiosulphate, preferably in situ.

A further process for the manufacture of compounds of the formula I in which the radical R₃ represents a group of the formula Ia in which R₁' represents a radical R₁, R₂' represents a radical R₂ and m represents O is characterised in that a compound of the formula

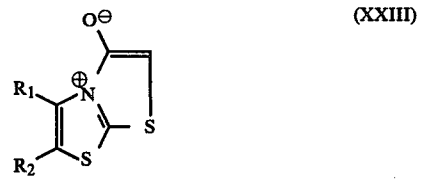

is subjected to treatment with a base, rearrangement taking place to form a corresponding compound of the formula I in which R₄ in the radical R₃ represents 1,3-(2- oxo)-propylene, and if necessary, a mixture of isomers obtainable according to the process is separated into the pure isomers and, if desired, a compound obtainable according to the process is converted into a different compound of the formula I and/or a free compound obtainable according to the process is converted into a salt or a salt obtainable according to the process is converted into the free compound.

Bases suitable for the treatment are, for example, organic nitrogen bases, preferably tertiary organic nitrogen bases, such as tri-lower alkylamines, for example triethylamine, or especially aromatic tertiary nitrogen bases, for example pyridine. The treatment with a base is effected preferably in an inert solvent or in an excess of the base used, if necessary while cooling or heating and/or under an inert gas atmosphere, such as a nitrogen atmosphere.

The starting materials of the formula XXIII exhibit the same pharmacological properties as the compounds of the formula I and have a comparable intensity of action. The invention relates also preferably to these, and to processes for their manufacture, to pharmaceutical compositions that contain them and to their use. These compounds can be manufactured by cyclising a compound of the formula

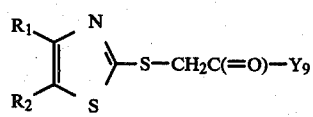

(XXIV)

in which $Y_9$ represents a removable radical.

Removable radicals $Y_9$ are, for example, optionally esterified hydroxy groups, such as hydroxy esterified by inorganic acids or acidic anhydrides or acidic esters thereof, such as halogen, halosulphenyl, halosulphonyl, dihalophosphono and the like, and also hydroxy esterified by carboxylic acids, such as organic carboxylic acids or semiesters or semianhydrides of carbonic acid or thio- or dithio-carbonic acid, for example lower alkanoyloxy, lower alkoxycarbonyloxy, halocarbonyloxy or halothiocarbonyloxy.

Cyclisation is effected in customary manner, advantageously by forming in situ a compound of the formula XXIV in which $Y_9$ represents hydroxy esterified as indicated, by reaction of the corresponding acid with a suitable acid anhydride, such as phosgene, phosphorus pentachloride, thionyl chloride, thiophosgene, a chloroformic acid lower alkyl ester, a lower alkanoyl chloride or, preferably, a lower alkanoic acid anhydride, and cyclising without isolation, if necessary in the presence of a basic condensation agent, such as an organic nitrogen base, such as, for example, a tri-lower alkylamine or pyridine, and/or while heating.

A preferred embodiment is characterised in that an acid of the formula XXIV, or a salt thereof, is treated with an acid anhydride, for example with acetic anhydride, if necessary in the presence of a basic condensation agent, for example in the presence of triethylamine.

The novel compounds of the formula I can also be manufactured by, in a compound of the formula

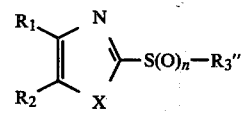

(XXV)

in which $R_3''$ represents a radical that can be converted into a group $R_3$ converting $R_3''$ into the desired group $R_3$, and, if necessary, separating a mixture of isomers obtainable according to the process into the pure isomers and, if desired, converting a compound obtainable according to the process into a different compound of the formula I and/or converting a free compound obtainable according to the process into a salt or a salt obtainable according to the process into the free compound.

Radicals that can be converted into radicals $R_3$ are, for example, radicals $R_3$ substituted by carboxy, especially 1-carboxy-2-oxo-lower alkyl radicals or radicals of the formula $-C(=O)-O-R_3$. The conversion of these radicals into radicals $R_3$ is effected by removing carbon dioxide.

Carbon dioxide can be removed in customary manner, for example by the action of acid, such as treatment with a protonic acid, such as a mineral acid, for example hydrochloric or sulphuric acid, advantageously in a solvent or diluent, and, if necessary, while heating, for example at approximately 50° to approximately 250° C.

Thus, compounds of the formula XXV in which $R_3''$ represents a 1-carboxy-2-oxo-lower alkyl radical can be converted into compounds of the formula I in which $R_3$ represents a 2-oxo-lower alkyl radical by heating with aqueous acid solutions, for example with equal parts of approximately 15% strength hydrochloric acid and acetic acid at approximately 60° to 100° C.

It is also possible to convert compounds of the formula XXV in which $R_3''$ represents a radical of the formula $-C(=O)-O-R_3$ into corresponding compounds of the formula I by heating with hydrogen chloride in tetrahydrofuran at approximately 40° to 80° C. with the removal of carbon dioxide.

Further radicals $R_3''$ that can be converted into radicals $R_3$ are, for example, carboxy-lower alkyl radicals of the formula $-C_nH_{2n}-COOH$, which are optionally in an ester, anhydride or salt form and can be reduced to oxo-lower alkyl radicals of the formula $-C_{n+1}H_{2n+1}=O$ or hydroxy-lower alkyl radicals of the formula $-C_{n+1}H_{2n+2}-OH$ carrying the oxo or hydroxy group in the ω-position.

The reduction is effected in customary manner, for example by reaction with a hydride transfer agent that transfers hydrogen in anionic form to the carbon atom in the α-position, for example with a light metal hydride or di-light metal hydride, for example with borohydride etherate, or preferably with lithium aluminium hydride, advantageously in an ether, such as a di-lower alkyl or lower alkylene ether, for example in diethyl ether, tertiary butoxymethane or tetrahydrofuran, or by means of sodium borohydride or sodium cyano-borohydride, advantageously in alcoholic solution. It is also possible to use reducing agents that transfer the non-valent metals or atomic hydrogen. These principles are utilised, for example, in metallic reduction, which can be effected by the action of finely divided metals, for example zinc powder, and similarly in reduction with nascent hydrogen, which can be produced, for example, by the action of acid on base metals, such as acetic acid on zinc, hydrochloric acid on iron, or the action of water on sodium amalgam. By using the above-mentioned reducing agents there are obtained preferably compounds of the formula I in which $R_3$ represents a hydroxy-lower alkyl radical. Salt forms of carboxy are, for example, basic salt forms, such as alkali or alkaline earth metal salt forms, but may also be ammonium salt forms with ammonia or organic amines. Anhydride forms are, for example, mixed anhydride forms with hydrohalic acids, but may also be mixed anhydride forms with organic carboxylic acids, such as lower alkanoic acids. Ester forms are, for example, lower alkyl ester forms, but may also be other organic ester forms, such as optionally substituted phenyl ester forms. As further ester forms there come into consideration lactone forms, for example γ-lactone forms, and when these are present in the ω-position and in a position lower than the (ω-2) position, radicals $R_3$ having two hydroxy groups are formed. The reduction of compounds of the formula XXV carrying radicals $R_3''$ that have a carboxy group in a salt, anhydride or ester form may, however, also be halted at the oxo stage falling within the scope of the formula I by using selective reducing agents. These are, for the reduction of carboxy that is optionally present in salt form, for example, mono- or di-lower alkyl borohydrides, for example 2-(2,3-dimethylbutyl)borohydride, for the reduction of anhydride forms, for example hydrogen in the presence of palladium or hydrocyanic acid in the presence of tertiary aromatic nitrogen bases, such as quinoline, and for the reduction of ester forms, for example electro-negatively substituted aluminium hydrides or alkali metal aluminium hydrides, for example N-methylpiperazin-1-yl aluminium hydride or sodium bis-(2-methoxyethoxy)-aluminium hydride, but also dibutylaluminium hydride.

As further reducing agents for the reduction of carboxy groups that are optionally present in a salt, anhydride or ester form to form oxo or hydroxy groups there come into consideration organo transfer agents that transfer an organic radical in anionic form to the carbon atom in the α-position, for example organometal compounds, such as compounds of aliphatic, araliphatic, or cycloaliphatic organic compounds of the formula $R_o$—H (XXVI) with metals, for example compounds of the formula $R_o$—$M^I$, $R_o$—$M^{II}$—Hal or $(R_o)_2M^{II}$, in which $M^I$ is a metal atom of the group 1A and $M^{II}$ is a metal atom of the groups 2A and 2B of the Periodic System of Elements, and $M^I$ preferably represents sodium or lithium and $M^{II}$ preferably represents magnesium or cadmium. Reduction with these reducing agents, in which carboxy groups that are present in a salt, anhydride or ester form are converted into tertiary hydroxy groups, is effected in customary manner, for example in an inert solvent, such as a di-lower alkyl or lower alkylene ether, for example in diethyl ether or tetrahydrofuran, if necessary while cooling or heating and/or under an inert gas atmosphere, such as a nitrogen atmosphere. In this case too, the reduction of a carboxy compound that is optionally in a salt, anhydride or ester form can, if desired, be stopped at the oxo stage by using mild reducing agents, for example a cadmium or halocadmium compound or a halomagnesium compound in the presence of a cadmium halide, or by carrying out the operation at low temperatures, for example at below −25° C.

Further radicals $R_3''$ that can be reduced to a group $R_3$ having at least one hydroxy group bonded to a saturated carbon atom are, for example, radicals $R_3''$ containing at least one hydroxy group etherified by an α-phenyl-lower alkanol or esterified by a carboxylic acid, such as a lower alkanoic acid or by carbonic acid or a semiester or semiamide thereof, such as optionally substituted benzyloxy, optionally halogenated lower alkanoyloxy or lower alkoxycarbonyloxy, benzyloxycarbonyloxy, di-lower alkylcarbamyloxy or carbonyldioxy. As such radicals $R_3''$ there come into consideration, for example: optionally substituted mono- or di-benzyloxy-lower alkyl, optionally halogenated mono- or di-lower alkanoyloxy-lower alkyl or mono- or di-lower alkoxycarbonyloxy- or carbonyldioxy-lower alkyl, each carrying the benzyloxy, benzyloxycarbonyloxy, the optionally halogenated lower alkanoyloxy or lower alkoxycarbonyloxy group(s) or the carbonyldioxy group in a position higher than the α-position, and also corresponding groups derived from groups of the formula Ia, that in place of $R_4$ contain a benzyloxy-, optionally halogenated lower alkanoyloxy- or lower alkoxycarbonyloxy- or benzyloxycarbonyloxy-lower alkylene, each carrying the benzyloxy, optionally halogenated lower alkanoyloxy or lower alkoxycarbonyloxy or benzyloxycarbonyloxy group in a position higher than the α-position and lower than the ω-position. Also coming into consideration are radicals $R_3''$ of the formula

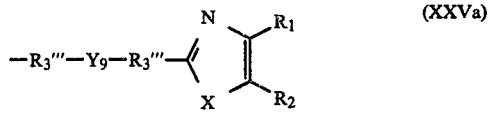

(XXVa)

in which $R_3'''$ represents a divalent aliphatic, cycloaliphatic or cycloaliphatic-aliphatic hydrocarbon radical that is substituted by oxy and, in addition, optionally by the substituents indicated and carries the oxy group in a position higher than the α-position, and $Y_9$ represents carbonyl or thiocarbonyl. As reducing agents for the reduction of α-phenyl-lower alkoxy and α-phenylalkoxycarbonyloxy groups and radicals of the formula XXVa, there come into consideration, for example, hydrogen in the presence of a hydrogenation catalyst, such as platinum or palladium, it being advantageous to carry out the operation in an inert solvent, if necessary at elevated pressure and/or while cooling or heating. Hydroxy groups esterified by carboxylic acids, and also α-phenyl-lower alkoxycarbonyloxy groups can be reduced, for example, by means of di-light metal hydrides, for example with lithium aluminium hydride.

2-Halo-lower alkoxycarbonyloxy (optionally after converting a 2-bromo-lower alkoxycarbonyloxy group into a 2-iodo-lower alkoxycarbonyloxy group), aroylmethoxycarbonyloxy or 4-nitrobenzyloxycarbonyloxy can be removed, for example, by treatment with a suitable chemical reducing agent, such as zinc in the presence of a suitable carboxylic acid, such as aqueous acetic acid. Aroylmethoxycarbonyloxy can also be cleaved by treatment with a nucleophilic, preferably salt-forming, reagent, such as sodium thiophenolate, and 4-nitrobenzyloxycarbonyloxy can be cleaved also by treatment with an alkali metal dithionite, for examples sodium dithionite.

Further radicals $R_3''$ are radicals that can be oxidised to form a group $R_3$ having at least one oxo or hydroxy group bonded to a saturated carbon atom, for example radicals $R_3''$ having at least one non-aromatic C—C double bond that, in customary manner, can be dihydroxylated at the double bond, for example by the action of an oxidising metal oxide or salt of an oxidising metal acid, or can be cleaved to form a radical $R_3$ that contains oxo or can be mono-hydroxylated by reaction with diborane and subsequent treatment with hydrogen peroxide. As oxidising metal oxides there come into consideration, for example, chromium trioxide or osmium tetroxide and as a salt of an oxidising metal acid, for example potassium permanganate. Oxidation with these agents and the reaction with diborane and subsequent treatment with hydrogen peroxide is effected in customary manner, advantageously in an inert solvent, if necessary while cooling or heating and/or under an inert gas atmosphere, for example a nitrogen atmosphere.

Further radicals $R_3''$ are radicals that can be solvolysed to form a group $R_3$ containing at least one hydroxy group bonded to a saturated carbon atom, for example radicals $R_3''$ that contain at least one esterified hydroxy group, at least one silyl group or a mono- or di-aryl-lower alkylidenedioxy or mono- or di-aryl-lower alkylidenedithio group, and also radicals of the formula XXVa in which $Y_9$* represents carbonyl, thiocarbonyl, di-lower alkoxy- or di-lower alkylenedioxymethylene or lower alkylidene, mono- or di-aryl-lower alkylidene or cycloalkylidene.

*Translator's note: Although "$Y_9$" does not appear in the German text, it has been assumed that this is what was intended.

Esterified hydroxy groups are, for example, halogen atoms that are converted, preferably by reaction with a salt of an organic carboxylic acid, such as sodium acetate, into organic acyloxy, such as acetoxy, but especially acyloxy groups. In mono- or di-aryl-lower alkylidenedioxy or mono- or diaryl-lower alkylidenedithio radicals aryl represents preferably phenyl which can also be substituted, for example, by lower alkyl, lower alkoxy and/or halogen.

Acyloxy groups are, for example, acyloxy groups derived from an alkanecarboxylic acid that is substituted by halogen or aryl, or from a benzoic acid that is optionally substituted, for example, by halogen, lower alkoxy or nitro, or from a carbonic acid semiester. Such acyloxy groups are, for example, halo-lower alkanoyloxy, such as 2-haloacetoxy, especially 2-chloro-, 2-bromo-, 2-iodo-, 2,2,2-trifluoro- or 2,2,2-trichloroacetoxy, benzyloxy optionally substituted, for example, by halogen, lower alkoxy or nitro, for example benzoyloxy, 4-chlorobenzoyloxy, 4-methoxybenzoyloxy or 4-nitrobenzoyloxy, or lower alkoxycarbonyloxy that is branched in the 1-position of the lower alkyl radical or suitably substituted in the 1- or 2-position, especially tert.-lower alkoxycarbonyloxy, for example tert.-butoxycarbonyloxy, arylmethoxycarbonyloxy having one or two aryl radicals that are preferably phenyl optionally mono- or poly-substituted, for example, by lower alkyl, especially tert.-lower alkyl, such as tert.-butyl, lower alkoxy, such as methoxy, hydroxy, halogen, for example chlorine, and/or by nitro, such as optionally substituted benzyloxycarbonyloxy, for example 4-nitrobenzyloxycarbonyloxy, or substituted diphenylmethoxycarbonyloxy, aroylmethoxycarbonyloxy in which the aroyl groups are preferably benzoyl optionally substituted, for example, by halogen, such as bromine, for example phenacryloxycarbonyloxy, 2-halo-lower alkoxycarbonyloxy, for example 2,2,2-trichloroethoxycarbonyloxy, 2-bromoethoxycarbonyloxy or 2-iodoethoxycarbonyloxy, or 2-(tri-substituted silyl)-ethoxycarbonyloxy in which the substituents, independently of one another, each represent an aliphatic, araliphatic, cycloaliphatic or aromatic hydrocarbon radical optionally substituted, for example, by lower alkyl, lower alkoxy, aryl, halogen or nitro and having, for example, up to 15 carbon atoms, such as corresponding optionally substituted lower alkyl, phenyl-lower alkyl, cycloalkyl or phenyl, for example 2-tri-loweralkylsilylethoxycarbonyloxy, such as 2-trimethylsilylethoxycarbonyloxy or 2-(di-n-butyl-methyl-silyl)-ethoxycarbonyloxy, or 2-triarylsilylethoxycarbonyloxy, such as 2-triphenylsilylethoxycarbonyloxy.

Hereinbefore and hereinafter aryl radicals represent preferably phenyl which can be substituted, for example, as indicated for $R_1$ and $R_2$ and/or by nitro.

Further acyl radicals are also corresponding radicals of organic phosphoric, phosphonic or phosphinic acids, such as di-lower alkylphosphoryloxy, for example dimethylphosphoryloxy, diethylphosphoryloxy, di-n-propylphosphoryloxy or diisopropylphosphoryloxy, dicycloalkylphosphoryloxy, for example dicyclohexylphosphoryloxy, optionally substituted diphenylphosphoryloxy, for example diphenylphosphoryloxy, optionally substituted, for example nitro-substituted, diphenyl-lower alkylphosphoryloxy, for example dibenzylphosphoryloxy or di-4-nitrobenzylphosphoryloxy, optionally substituted phenoxyphenylphosphonyloxy, for example phenoxyphenylphosphonyloxy, di-lower alkylphosphinyloxy, for example diethylphosphinyloxy, or optionally substituted diphenylphosphinyloxy, for example diphenylphosphinyloxy.

A silyloxy group is especially an organic silyloxy group in which the silicon atom has as substituents preferably lower alkyl, especially methyl, also lower alkoxy, for example methoxy, and/or halogen, for example chlorine. Corresponding silyloxy groups are especially tri-lower alkylsilyloxy, especially trimethylsilyloxy, also dimethyl-tert.-butyl-silyloxy, lower alkoxy-lower alkyl-halosilyloxy, for example methoxymethyl-chloro-silyloxy, or di-lower alkyl-halosilyloxy, for example dimethyl-chlorosilyloxy.

The mentioned radicals $R_3''$ containing groups that can be solvolysed to form hydroxy groups are, for example, mono- or di-acyl-lower alkyl, mono- or di-silyloxy-lower alkyl, mono- or di-aryl-lower alkylidenedioxy-lower alkyl or mono- or di-aryl-lower alkylidenedithio-lower alkyl, each carrying the acyloxy group(s), silyloxy group(s), mono- or di-aryl-lower alkylidenedioxy group or mono- or di-aryl-lower alkylidenedithio group in a position higher than the α-position, and also radicals of the formula XXVa in which $R_3'''$ represents oxy-lower alkylene carrying the oxo group in a position higher than the α-position and $Y_9$ represents carbonyl or thiocarbonyl, and also corresponding radicals derived from groups of the formula Ia that contain as or in place of $R_4$ mono- or di-acyloxy-lower alkylene, mono- or di-silyloxy-lower alkylene, lower alkylidene- or mono- or di-aryl-lower alkylidenedioxy-lower alkylene or lower alkylidene- or mono- or di-aryl-lower alkylidene-dithio-lower alkylene, each carrying the acyloxy group(s), silyloxy group(s), lower alkylidenedioxy or mono- or di-aryl-lower alkylidenedioxy group or lower alkylidenedithio or mono- or di-aryl-lower alkylidenedithio group in a position higher than the α-position and lower than the ω-position.

The solvolysis is effected, for example, by hydrolysis (treatment with water), alcoholysis (treatment with an alcohol) or ammonolysis or aminolysis (treatment with ammonia or with an organic amine).

Hydrolysis is carried out in customary manner, if necessary in the presence of a hydrolysing agent and/or an inert solvent, while cooling or heating and/or under an inert gas atmosphere. Hydrolysing agents are, for example, acidic or alkaline agents. Acidic agents are, for example, mineral acids, hydrohalic acids, for example hydrochloric, hydrobromic or hydriodic acid, or oxyacids of sulphur or phosphorus, or acidic salts thereof, such as sulphuric acid, potassium bisulphate or phosphoric acid, or organic carboxylic or sulphonic acids, for example lower alkanoic acids, such as acetic acid, trifluoroacetic acid or chloroacetic acid, or p-toluenesulphonic acid. Basic agents are, for example, hydroxides or carbonates of alkali or alkaline earth metals, such as potassium, sodium or calcium hydroxide, or potassium or sodium carbonate. Inert solvents are, for example, polar water-miscible solvents, such as alcohols, for example methanol or ethanol, lower alkylene ethers, such as dioxan, di-lower alkylketones, such as acetone, tertiary amides, for example dimethylformamide, N-methylpyrrolidone or hexamethylphosphoric acid triamide, or di-lower alkyl sulphoxides, for example dimethyl sulphoxide.

By means of alcoholysis it is possible to free especially hydroxy groups esterified by organic carboxylic acids by transesterification. Transesterification is effected in customary manner, for example in the presence of an acidic or basic agent, if necessary while cooling or heating and/or under an inert gas atmosphere, for example a nitrogen atmosphere. As acidic and basic agents there come into consideration, for example, those mentioned, and as basic agents also metal alcoholates, such as alkali metal or alkaline earth metal lower alkoxides, for example sodium methoxide.

It is also possible, however, to free the hydroxy group from the mentioned acyloxy groups by aminolysis. Aminolysis is effected in customary manner, if necessary while cooling or heating and/or under an inert gas atmosphere, for example a nitrogen atmosphere.

2-Halo-lower alkanoyloxy can also, however, firstly be converted into the isothiuronium derivative by reaction with thiourea and then cleaved by hydrolysis or alcoholysis of the isothiuronium derivative. 2-Substituted silylethoxycarbonyloxy can be cleaved advantageously by treatment with an alkali metal fluoride, for example with potassium fluoride. Phosphoro, phosphono or phosphino groups can be removed, for example, by treatment with a phosphorus-containing acid, such as a phosphoric, phosphonic or phosphinic acid, for example orthophosphoric acid or polyphosphoric acid, an acidic ester, for example monomethyl, monoethyl, dimethyl or diethyl phosphate, or monomethylphosphonic acid, or an anyhydride thereof, such as phosphorus pentoxide.

The starting materials can be manufactured according to methods known per se, for example by removing HY from compounds of the formula

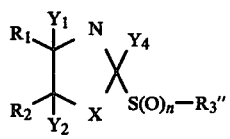

(XXVII)

in which $Y_1$, $Y_2$, $Y_3$ and $Y_4$ have the meanings given under formula II, by reaction of compounds of the formulae

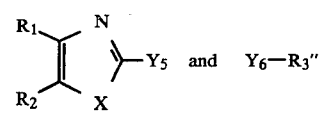

(XVI)       (XVIII)

in which one of the radicals $Y_5$ and $Y_6$ represents a reactive esterified hydroxy group and the other represents a group of the formula $-S(O)_n-$ or $-S-SH$ that is present in salt form or, if $R_3''$ contains α-phenyl-lower alkoxy, mono- or di-aryl-lower alkylidenedioxy, mono- or di-aryl-lower alkylidenedithio or silyloxy, or represents a group of the formula XXVa in which $Y_9$ represents lower alkylidene, mono- or di-aryl-lower alkylidene or cycloalkylidene, one of the radicals $Y_5$ and $Y_6$ represents a metallic radical and the other represents a reactive esterified hydroxy group or, if n represents 1 or 2, etherified hydroxy or, if n represents 0, etherified mercapto.

Compounds of the formula XXV in which $R_3''$ contains acyloxy groups bonded at vicinal carbon atoms, preferably acyloxy groups that are derived from organic carboxylic acids, such as lower alkanoyloxy, may also be manufactured by oxidative acyloxylation of the double bond in corresponding compounds of the formula I or XXV that have (a) non-aromatic double bond(s). The oxidative acyloxylation is effected, for example, by treatment with a heavy metal salt of an organic carboxylic acid, for example with lead tetraacetate, or with a silver salt of an organic carboxylic acid in the presence of halogen, for example with silver acetate in the presence of iodine or bromine.

Compounds of the formula I that can be obtained according to the process or according to other procedures not mentioned above can be converted into different compounds of the formula I in a manner known per se.

Thus, for example, optionally etherified or esterified hydroxy groups can be converted into one another.

If, for example, at least one of the radicals $R_1$, $R_2$ and $R_3$ contains a hydroxy group, this hydroxy group may be etherified in the usual manner. Thus, hydroxy as a component of $R_3$ can be converted into a corresponding lower alkoxy group by means of a lower alkylating agent, such as a lower alkanol, for example methanol, in the presence of an acid, such as a mineral acid, for example sulphuric acid, or a dehydrating agent, such as dicyclohexyl carbodiimide, and hydroxy in a radical $R_1$ or $R_2$ can be converted into a corresponding alkoxy group, for example, in the presence of bases, such as alkali metal hydroxides or carbonates, for example sodium hydroxide or potassium carbonate, with the aid of di-lower alkyl sulphates or diazo-lower alkanes. Conversely, ethers, such as lower alkoxy groups, as substituents of $R_1$ and $R_2$, may be removed, for example, by treatment with acids, such as Lewis acids, for example boron tribromide, or mineral acids, for example hydrogen iodide.

Furthermore, hydroxy may be esterified, for example converted into lower alkanoyloxy, for example by reaction with a corresponding lower alkanecarboxylic acid, such as acetic acid, or a reactive derivative, such as a symmetric anhydride, thereof, or an anhydride with a hydrohalic acid, if necessary in the presence of a condensation agent, when using anhydrides as starting material, for example in the presence of a basic condensation agent, such as an alkali metal hydroxide or carbonate, or a tertiary nitrogen base, for example a tri-lower alkylamine or pyridine, and when using an acid as starting material, for example in the presence of an acid, such as a protonic acid, for example hydrochloric acid, sulphuric acid, phosphoric acid or a sulphonic acid, or a Lewis acid, for example boron trifluoride etherate.

It is also possible in compounds of the formula I to N-oxidise radicals $-S(O)_n-$ and/or $-S(O)_m-$ in which n and m represent 0 to form the corresponding sulphinyl or sulphonyl radicals in which n and m represent 1 or 2, and to N-oxidise radicals $-S(O)_n-$ and/or $-S(O)_m-$ in which n and m represent 1 to form the corresponding sulphonyl radicals in which n represents 2 and/or to N-oxidise heteroaryl radicals $R_1$, $R_2$, $R_1'$ and/or $R_2'$ having at least one free ring nitrogen atom, such as pyridyl radicals. The oxidation is preferably effected by the action of a suitable oxidising agent, advantageously in a solvent that is inert towards this oxidising agent, if necessary while cooling or heating, for example in a temperature range of approximately $-30°$ to $+100°$ C., preferably at approximately $0°$ to $60°$ C., in a closed vessel and/or under an inert gas atmosphere, such as a nitrogen atmosphere. Suitable oxidising agents are, for example, peroxy compounds, such as hydrogen peroxide, organic hydroperoxides, for example tert.-butyl hydroperoxide, organic peracids, such as aromatic or aliphatic percarboxylic acids, for example m-chloroperoxybenzoic acid, peroxyacetic acid or permonophthalic acid, oxidising heavy metal compounds, such as chromium(VI) or manganese(IV) or manganese(VII) compounds, for example chromium trioxide, chromic acid, manganese dioxide or potassium permanganate, oxidising inorganic oxyacids, such as oxyacids of nitrogen, of halogens or chalcogens, or anhydrides or salts thereof, for example nitric acid, dinitrogen tetroxide, selenium dioxide or sodium metaperiodate, and also ozone. Suitable solvents are, for example, halogenated hydrocarbons, such as haloalkanes, for example carbon tetrachloride, chloroform or methylene chloride, or carboxylic acids, such as alkanoic acids, for example acetic acid, or anhydrides thereof.

In a preferred form of this oxidation process, for example, thioethers of the formula I in which n and m represent 0 and/or a radical $R_1$, $R_2$, $R_1'$ and/or $R_2'$ contain(s) an unsubstituted ring nitrogen atom, can be oxidised to form the corresponding sulphinyl or sulphonyl compounds in which n and/or m represent(s) 1 or 2, and, if desired, oxidised at the nitrogen atom, by reaction with an organic peracid, for example with m-chloroperbenzoic acid, in a haloalkane, for example in chloroform.

In another preferred form of this process it is possible selectively to oxidise thioethers of the formula I in which n and/or m represent(s) 0 by treatment with sodium metaperiodate, preferably in a haloalkane, for example in carbon tetrachloride or chloroform, to form the corresponding sulphoxides in which n and/or m represent(s) 1, or to oxidise these with hydrogen peroxide in acetic acid to form sulphones in which n and/or m represent(s) 2.

Conversely, in compounds of the formula I in which n and/or m represent(s) 1 or 2 and/or heteroaryl radicals $R_1$, $R_2$, $R_1'$ and/or $R_2'$ are N-oxidised, the group $-S(O)-$ or $-S(O)_2$ can be reduced to form thio and-/or N-oxidised ring nitrogen. The reduction is effected by treatment with customary reducing agents, for example with nascent or catalytically activated hydrogen, such as iron or zinc and acid, such as hydrochloric acid, or with hydrogen in the presence of Raney nickel, advantageously in an inert solvent, such as a lower alkanol, or with light metal hydrides or di-light metal hydrides, for example with alkali metal aluminium hydrides or alkali metal borohydrides, for example with sodium borohydride or lithium aluminium hydride, advantageously in an inert solvent, such as an ether, for example diethyl ether or tetrahydrofuran, or, for selective reduction of N-oxide groups, with a phosphorus-(III) compound, such as a phosphine, for example triphenylphosphine or tri-n-butylphosphine, or a phosphorous acid ester, such as a tri-lower alkylphosphite, for example with trimethyl- or triethyl-phosphite.

Furthermore, it is possible optionally to introduce additional carbon substituents into the radicals $R_1$, $R_2$, $R_1'$ and/or $R_2'$. Thus, halogenation can be effected in customary manner, for example by reaction with chlorine or bromine in the presence of iron or by means of N-chlorosuccinimide. It is also possible to carry out alkylation in customary manner, for example by reaction with an alkyl halide, alkanol or alkene in the presence of aluminium trichloride. It is also possible to carry out nitration in customary manner, for example by means of nitric acid/sulphuric acid, to reduce the nitro group, for example with tin(II) chloride to form amino and to convert this by means of sodium nitrite and tetrafluoroboric acid into fluorine; by means of hydrochloric acid, sodium nitrite and copper(I) chloride (bromide) via chlorine (bromine), or by means of sodium nitrite and potassium iodide via iodine or by means of sodium nitrite and a lower alkylmercaptan via lower alkylthio or by means of sodium nitrite, into hydroxy.

It is also possible in radicals $R_3$ that contain oxo to reduce oxo to hydroxy or to replace it reductively by hydrogen, for example by the action of nascent hydrogen, produced, for example by treating base metals with proton donors, for example treating zinc with hydrochloric or acetic acid, amalgamated aluminium or sodium amalgam with water or sodium with an alcohol, such as methanol. The reductive replacement of oxo by hydrogen can also be effected by reaction with hydrazine in the presence of a metal base, for example sodium or potassium hydroxide, or in the presence of an alkali metal alcoholate, such as sodium methoxide, in a high-boiling alcohol, such as ethylene glycol, diethylene glycol or diethylene glycol monomethyl ether, preferably at elevated temperature, for example at approximately $150°$ to $250°$ C. Oxo can also be reduced to hydroxy in customary manner, for example by reaction with a light metal hydride, such as borane/tetrahydrofuran or diborane, or a di-light metal hydride, such as sodium borohydride, sodium cyanoborohydride or lithium aluminium hydride, or by reaction with a secondary alcohol, such as isopropanol or cyclohexanol, in the presence of an aluminium alcoholate. The reduction of oxo to hydroxy can, however, also be effected with the simultaneous introduction of a hydrocarbon radical at the carbonyl carbon atom by reaction with a lower alkyl metal compound, for example with a lower alkyl lithium or lower alkyl magnesium halide. In analogous manner it is also possible to introduce a radical that contains oxo in the $\beta$-position by the aldol addition of a ketone or aldehyde to an aldehydic oxo group with reduction of the oxo group to form hydroxy. It is also possible to convert oxo into di-lower alkoxy, lower alkylenedioxy, di-lower alkylthio or lower alkylenedithio by treatment with an orthocarboxylic acid ester, for example an orthoformic acid lower alkyl ester or, under conditions that remove water and with acid catalysis, with a lower alkanol, lower alkanediol, lower alkylmercaptan or lower alkyldimercaptan. It is likewise possible to convert aldehydes of the formula I in which $R_3$ contains a ω-oxo group into the bisulphite addition products in which $R_3$ contains a ω-hydroxy group and a ω-sulpho group that is present in salt form by reaction with a metal bisulphite, for example with sodium bisulphite.

Furthermore, in radicals $R_3$ that contain hydroxy it is possible to replace the hydroxy group(s) reductively by hydrogen, for example as indicated above for the reductive replacement of oxo by the action of hydrogen. Hydroxy can also be oxidised to oxo by reaction with an oxidising heavy metal compound, for example with silver acetate or bismuth oxide, with dimethyl sulphoxide in the presence of trifluoromethanesulphonic acid anhydride or N-chlorosuccinimide, or with a cyclohexanone, in the presence of an aluminium alcoholate, such as aluminium isopropylate. It is also possible to convert hydroxyalkyl $R_3$ into alkenyl or lower alkoxyalkenyl by acid treatment with the removal of water, or into alkyl by acid hydrolysis.

In radicals $R_3$ it is also possible to hydrolyse, preferably by acid catalysis, geminally bonded di-lower alkoxy, di-lower alkylthio, lower alkylenedioxy and lower alkylenedithio to form oxo, or lower alkyl containing vicinally bonded lower alkylenedioxy to form di-hydroxy-lower alkyl.

Stereoisomeric mixtures that can be obtained according to the invention can be separated into their components in customary manner.

Thus, diastereoisomeric mixtures can be separated into their components on the basis of differences in the physical properties of the components by customary physical separating processes, such as crystallisation, chromatography distillation or phase distribution processes.

Enantiomeric mixtures, such as racemates, can be separated into the enantiomers by crystallisation from optically active solvents, by chromatography on optically active solids, by the action of micro-organisms or by reaction with an optically active auxiliary compound to form diastereoisomeric mixtures, for example with an optically active acid, to form mixtures of diastereoisomeric acid addition salts, and by separation of these into the diastereoisomers from which the enantiomers can be freed in the customary manner. Optically active acids customary for this purpose are, for example, D- or L-tartaric acid, di-o-toluyltartaric acid, malic acid, mandelic acid, camphorsulphonic acid or quinic acid.

Resulting free compounds can be converted into acid addition salts in a manner known per se, for example by reacting a solution of the free compound in a suitable solvent or solvent mixture with one of the afore-mentioned acids, or with a solution thereof, or with a suitable anion exchanger.

Resulting acid addition salts can be converted into the free compounds in a manner known per se, for example by treatment with a base, such as an alkali metal hydroxide, a metal carbonate or bicarbonate, or ammonia, or with a suitable anion exchanger.

Resulting acid addition salts can be converted into different acid addition salts in a manner known per se, for example by treating a salt of an organic acid with a suitable metal salt, such as a sodium, barium or silver salt of an acid in a suitable solvent in which an inorganic salt being formed is insoluble and therefore separates out of the reaction mixture.

The compounds, including their salts, can be obtained also in the form of hydrates or can include the solvent used for crystallisation.

As a result of the close relationship between the novel compounds in free form and in the form of their salts, hereinbefore and hereinafter the free compounds or their salts shall be understood to mean optionally also the corresponding salts or free compounds, respectively, where appropriate with regard to meaning and purpose.

The invention relates also to those embodiments of the process in which compounds obtainable as intermediates at any stage of the process are used as starting materials and the remaining process steps are carried out, or in which a starting material is formed under the reaction conditions or is used in the form of a derivative, where applicable in the form of a salt.

In the process of the present invention it is preferable to use those starting materials which result in the compounds described at the beginning as being especially valuable. The present invention relates also to novel starting materials and to processes for their manufacture.

Compounds of the formula XXIII mentioned as starting materials exhibit the same pharmacological properties as compounds of the formula I and have a comparable intensity of action; they can therefore also be used as active ingredients in antirheumatic or anti-nociceptive medicaments.

Accordingly, the invention relates also to compounds of the formula XXIII, to processes for their manufacture, to compositions containing these compounds and to their use as active ingredients in medicaments, $R_1$ and $R_2$ having especially the meanings given for the compounds of the formula I emphasised as being especially preferred at the beginning.

The pharmaceutical compositions according to the invention, which contain compounds of the formula I or pharmaceutically acceptable salts thereof, are for enteral, such as oral or rectal, and parenteral administration and also for topical application to (a) warm blooded animal(s) and contain the pharmacological active ingredient alone or together with a pharmaceutically acceptable carrier. The dosage of the active ingredient depends on the species of warm-blooded animal, age and individual condition, and on the method of administration.

In normal cases, the estimated approximate daily dose in the case of oral administration to a warm-blooded animal weighing approximately 75 kg is about 10–100 mg, advantageously divided into several equal partial doses.

The novel pharmaceutical compositions contain, for example, from approximately 10% to approximately 80%, preferably from approximately 20% to approximately 60%, of active ingredient. Pharmaceutical compositions according to the invention for enteral or parenteral administration are, for example, those in dosage unit forms, such as dragées, tablets, capsules or suppositories, and also ampoules. These are manufactured in a manner known per se, for example by means of conventional mixing, granulating, confectioning, dissolving, or lyophilising processes. For example, pharmaceutical compositions for oral use can be obtained by combining the active ingredient with solid carriers, optionally granulating a resulting mixture and processing the mixture or granulate, if desired or necessary after the addition of suitable adjuncts, to form tablets or dragée cores.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, maize, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical preparations for oral administration are dry-filled capsules consisting of gelatine and also soft sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical compositions there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances which increase the viscosity, for example sodium carboxymethylcellulose, sorbitol and/or dextran, and, optionally, also stabilisers.

There come into consideration as pharmaceutical compositions for topical use especially creams, ointments, pastes, foams, tinctures and solutions that contain from about 0.5% to about 20% of active ingredient.

Creams are oil-in-water emulsions that contain more than 50% of water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. As emulsifiers there come into consideration surface-active substances having predominantly hydrophilic properties, such as corresponding non-ionic emulsifiers, for example fatty acid esters of polyalcohols, or ethylene oxide adducts thereof, such as polyglycerine fatty acid esters or polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the aqueous phase are, inter alia, agents that reduce the drying out of the creams, for example polyalcohols, such as glycerine, sorbitol, propylene glycol and/or polyethylene glycols, also preservatives, perfumes etc.

Ointments are water-in-oil emulsions that contain up to 70%, but preferably from approximately 20% to approximately 50%, of water or aqueous phases. As oily phase there come into consideration especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerine, propylene glycol, sorbitol and/or polyethylene glycol, and also preservatives, perfumes etc.

Fatty ointments are anhydrous and contain as base especially hydrocarbons, for example paraffin, petroleum jelly and/or liquid paraffins, and also natural or partially synthetic fats, for example coconut fatty acid triglyceride, or preferably hardened oils, for example hydrogenated ground nut oil or castor oil, and also fatty acid partial esters of glycerine, for example glycerine mono- and di-stearate, and also, for example, the fatty alcohols, which increase the water-absorbing capacity, emulsifiers and/or additives mentioned in connection with the ointments.

Pastes are creams and ointments containing powder ingredients that absorb secretions, such as metal oxides, for example titanium oxide or zinc oxide, also talc and/or aluminium silicates, the purpose of which is to bind any moisture or secretions present.

Foams are administered from pressurised containers and are liquid oil-in-water emulsions in aerosol form, halogenated hydrocarbons, such as chlorofluoro-lower alkanes, for example dichlorodifluoromethane and dichlorotetrafluoroethane, being used as propellants. For the oily phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers having predominantly hydrophilic properties, such as polyoxyethylene sorbitan fatty acid esters (Tweens), and those having predominantly lipophilic properties, such as sorbitan fatty acid esters (Spans). In addition, there may be used customary additives, such as preservatives etc.

Tinctures and solutions generally have an aqueous ethanolic base to which there are added, inter alia, polyalcohols, for example glycerine, glycols, and/or polyethylene glycol, as humectants for reducing evaporation, and fat-restoring substances, such as fatty acid esters with lower polyethylene glycols, that is to say lipophilic substances that are soluble in the aqueous mixture, to replace the fatty substances that are taken from the skin by the ethanol, and, if necessary, other adjuncts and additives.

The pharmaceutical compositions for topical application are manufactured in a manner known per se, for example by dissolving or suspending the active ingredient in the base or, if necessary, in a part thereof. When processing the active ingredient in the form of a solution, it is usually dissolved in one of the two phases before emulsification; when processing the active ingredient in the form of a suspension, it is mixed with a part of the base after emulsification and then added to the remainder of the formulation.

The present invention relates also to the use of compounds of the formulae I and II and salts of such compounds having salt-forming properties, preferably for the treatment of inflammations, especially chronic inflammatory disorders of the rheumatic type, especially chronic arthritis.

The following Examples illustrate the invention described above but are not intended to limit the scope of the invention in any way. Temperatures are given in degrees Centigrade, pressures in mbar.

EXAMPLE 1

5 g of 4,5-bis-phenylthiazoline-2-thione are dissolved in 50 ml of hexamethylphosphoric acid triamide, the solution is cooled to 5° and, while stirring, sodium hydride (0.89 g of a 50% strength suspension in mineral oil, de-oiled with hexane) is added. The mixture is stirred for 30 minutes at room temperature, then 3.18 g of ethyl iodide are slowly added dropwise and the mixture is then stirred for 30 minutes at room temperature, poured onto 1000 ml of ice-water and extracted by shaking twice with diethyl ether. The ether phases are combined, washed with water, dried over magnesium sulphate and concentrated to dryness by evaporation. The remaining pale yellow oil is dissolved in 200 ml of toluene/hexane (1:1) and filtered through 10 g of silica gel. Concentration of the eluate by evaporation yields 2-ethylthio-4,5-bis-phenylthiazole in the form of an oil.

The starting material can be produced, for example, in the following manner: 22.48 g of 2-bromo-1,2-bis-phenylethanone are suspended in 90 ml of 95% strength ethanol and brought into solution by heating to 45°. The solution is cooled to 20°, 27 g of ammonium dithiocarbamate are added and the mixture is heated under reflux for 15 minutes. The mixture is then cooled in an ice-bath and the precipitate which forms is filtered with suction, then washed with cold ethanol, digested three times with water, filtered with suction again, dissolved in 2 N sodium hydroxide solution, filtered and precipitated with 2 N hydrochloric acid. The precipitated 4,5-bis-phenylthiazoline-2-thione is recrystallised from ethyl acetate. It melts at 224°–226°. The following are obtained in an analogous manner: 2-methylthio-4,5-bis-phenylthiazole, m.p. 73°–74° and 2-propylthio-4,5-bis-phenylthiazole, m.p. 35°–36°.

EXAMPLE 2

1.106 g of pyridine and 3.68 g of 2-bromo-1,2-bis-phenylethanone are added while stirring to a solution, cooled to 5°, of 1.694 g of ethyldithiocarbamate in 25 ml of ethanol. The mixture is then stirred for 30 minutes at 5° and for 90 minutes at room temperature, concentrated to dryness by evaporation under reduced pressure, and the residue is partitioned between methylene chloride and water. The aqueous phase is acidified with N hydrochloric acid and extracted by shaking again twice with methylene chloride. The organic phases are combined, dried over magnesium sulphate and concentrated to dryness by evaporation under reduced pressure. The remaining oil is purified by chromatography over 100 g of silica gel with toluene/hexane (1:1) as eluant. Concentration by evaporation yields 2-ethylthio-4,5-bis-phenylthiazole in the form of an oil.

EXAMPLE 3

4.93 g of 2-methoxycarbonylmethylthio-4,5-bis-phenylthiazole are added dropwise in the course of 30 minutes, while stirring, to a solution, cooled to from 0° to 5°, of 0.575 g of lithium aluminium hydride in 25 ml of diethyl ether. The mixture is then stirred for 1 hour, first of all 0.6 ml and then a further 50 ml of water are cautiously added, the mixture is acidified with N hydrochloric acid, the ether layer is separated off and the aqueous phase is subsequently washed with diethyl ether. The ethereal solutions are combined, dried over magnesium sulphate and concentrated to dryness by evaporation. The residue is dissolved in toluene and purified by chromatography over 90 g of silica gel. The fractions eluted with toluene/ethyl acetate are combined and concentrated by evaporation under reduced pressure. 2-(2-Hydroxyethylthio)-4,5-bis-phenylthiazole having a melting point of 77°–79° is obtained.

The starting material can be produced, for example, in the following manner: 6 g of 4,5-bis-phenylthiazoline-2-thione are dissolved in 50 ml of hexamethylphosphoric acid triamide, the solution is cooled to 5° and, while stirring, sodium hydride (0.89 g of a 50% strength suspension in mineral oil, de-oiled with hexane) is added. The mixture is stirred for 30 minutes at room temperature, 3.57 g of bromoacetic acid methyl ester are slowly added dropwise, the mixture is then stirred for 1 hour at room temperature, poured into 500 ml of ice-water, extracted by shaking twice with 300 ml of ethyl acetate each time, washed with water, dried over magnesium sulphate and concentrated to dryness by evaporation under reduced pressure. The remaining oil is dissolved in toluene and purified by chromatography over 50 g of silica gel. The eluate with toluene/ethyl acetate (95:5) is concentrated by evaporation under reduced pressure. 2-Methoxycarbonylmethyl-4,5-bis-phenylthiazole having a melting point of 65°–67° is obtained.

EXAMPLE 4

In a manner analogous to that described in Example 1 it is also possible to produce: 2-methylthio-4,5-bis-(p-chlorophenyl)-thiazole, m.p. 94°–95°, 2-ethylthio-4,5-bis-(p-chlorophenyl)-thiazole, m.p. 79°–81°, 2-propylthio-4,5-bis-(p-chlorophenyl)-thiazole, m.p. 63°–64°, and 2-(2-hydroxyethylthio)-4,5-bis-(p-chlorophenyl)-thiazole, m.p. 122°–124°.

The 4,5-bis-(p-chlorophenyl)-thiazoline-2-thione used as starting material can be produced, for example, by reacting 2-bromo-1,2-bis-(p-chlorophenyl)-ethanone with ammonium dithiocarbamate in a manner analogous to that described in Example 1. It melts at 241°–243°.

EXAMPLE 5

Sodium hydride (1.06 g of a 50% suspension in mineral oil, de-oiled with hexane) is added, while stirring, to a solution, cooled to 5°, of 6 g of 5-phenyl-4-(3-pyridyl)-thiazoline-2-thione in 40 ml of hexamethylphosphoric acid triamide. The internal temperature is increased to 10°, 3.15 g of methyl iodide are slowly added dropwise and the mixture is then stirred for 15 minutes at room temperature and poured into 500 ml of ice-water. The oil which separates crystallises out after being left to stand for some time. The crystals are taken up in ethyl acetate and the aqueous phase is then shaken twice with 100 ml of ethyl acetate each time. The organic phases are washed twice with 200 ml of water each time, combined, dried over magnesium sulphate and concentrated by evaporation under reduced pressure. The remaining oil is triturated with 30 ml of diethyl ether, whereupon crystallisation occurs. The crystalline 2-methylthio-5-phenyl-4-(3-pyridyl)-thiazole is filtered with suction. It melts at 95°–95°.

The starting material can be produced, for example, in the following manner:

120 g of 2-phenyl-1-(3-pyridyl)-ethanone hydrobromide are heated to 75° in 1000 ml of acetic acid. The heating bath is then removed and, while stirring, a solution of 75.8 g of bromine in 30 ml of acetic acid is added in portions each of 5 ml. While then stirring, the mixture is gradually allowed to cool to 60°, then is cooled to 20° by means of an ice-bath, filtered with suction, washed first once with 100 ml of cold acetic acid and then twice with 200 ml of diethyl ether each time, and dried under reduced pressure. 2-Bromo-2-phenyl-1-(3-pyridyl)-ethanone hydrobromide having a melting point of 216°–219° is obtained.

42.0 g of the 2-bromo-2-phenyl-1-(3-pyridyl)-ethanone hydrobromide so obtained are dissolved, while stirring, in 500 ml of methanol (95% strength), the solution is cooled to 10° and, in the course of 5 minutes, 14.93 g of ammonium dithiocarbamate are added in portions. The mixture is cooled for a further 5 minutes, the ice-bath is removed, after 45 minutes again 14.93 g of ammonium dithiocarbamate are added and the mixture is then heated at the boil for 90 minutes and concentrated to dryness by evaporation. The residue obtained by concentration by evaporation is digested with 200 ml of water and 65 ml of 2 N sodium hydroxide solution, filtered with suction and washed with a little water. The product is dissolved in 100 ml of 2 N sodium hydroxide solution, filtered and acidified to pH 5 with 2 N hydrochloric acid. The precipitated crystals are filtered with suction, washed twice with a little ice-water, sucked dry, and then thoroughly washed twice with 30 ml of acetone each time and then twice with 50 ml of diethyl ether each time. 5-Phenyl-4-(3-pyridyl)-thiazoline-2-thione having a melting point of 229°–232° is obtained.

EXAMPLE 6

Sodium hydride (1.06 g of a 50% strength suspension in mineral oil, de-oiled with hexane) is added, while stirring, to a solution, cooled to 5°, of 6 g of 5-phenyl-4-(3-pyridyl)-thiazoline-2-thione in 40 ml of hexamethylphosphoric acid triamide. 3.46 g of ethyl iodide are added dropwise thereto, and the mixture is then stirred for 15 minutes at room temperature and poured into 500 ml of ice-water. The oil which separates is taken up in 100 ml of ethyl acetate. The resulting solution is extracted six times with 50 ml of 2 N ammonium chloride solution each time. The extracts are combined, adjusted to pH 10 with sodium hydroxide solution, and extracted twice with 100 ml of ethyl acetate each time. The organic phases are combined, dried over magnesium sulphate and concentrated by evaporation to dryness under reduced pressure. The residue obtained by concentration by evaporation is dissolved in 30 ml of toluene and purified by chromatography over 30 g of silica gel. There crystallises from the eluate with toluene/ethyl acetate (10:1), after leaving to stand for some time in the refrigerating chamber, 2-ethylthio-5-phenyl-4-(3-pyridyl)-thiazole having a melting point of 41°–42°.

EXAMPLE 7

Sodium hydride (1.24 g of a 50% strength suspension in mineral oil, de-oiled with hexane) is added, while stirring, to a solution, cooled to 5°, of 7 g of 5-phenyl-4-(3-pyridyl)-thiazoline-2-thione in 40 ml of hexamethylphosphoric acid triamide. The internal temperature is increased to 10°, 4.45 g of 2-iodoethanol are added dropwise thereto, and the mixture is then stirred for 15 minutes at room temperature, poured into 500 ml of ice-water and extracted by shaking twice with 100 ml of ethyl acetate each time. The organic phases are combined, washed twice with 100 ml of 0.1 N sodium hydroxide solution each time, dried over magnesium sulphate and concentrated to dryness by evaporation under reduced pressure. The residue obtained by concentration by evaporation is brought to crystallisation by triturating with 30 ml of diethyl ether. Stirring is carried out for 1 hour and crystalline 2-(2-hydroxyethylthio)-5-phenyl-4-(3-pyridyl)-thiazole having a melting point of 109°–110° is filtered off with suction.

EXAMPLE 8

10 g of 4,5-bis-(p-methoxyphenyl)-thiazoline-2-thione are dissolved in 50 ml of hexamethylphosphoric acid triamide, the solution is cooled to 5° and, while stirring, sodium hydride (1.45 g of a 50% strength suspension in mineral oil, de-oiled with hexane) is added. The mixture is then stirred for 30 minutes at room temperature, 5.22 g of 2-iodoethanol are added dropwise thereto, and the mixture is then stirred for 15 minutes at room temperature and poured into a mixture of 30 ml of 2 N hydrochloric acid and 400 ml of ice-water. After being left to stand for some time the oil which separates crystallises and is taken up in 200 ml of methylene chloride. The solution is dried over magnesium sulphate and concentrated to dryness by evaporation. To crystallise, the residue is triturated with diethyl ether. 2-(2-hydroxyethylthio)-4,5-bis-(p-methoxyphenyl)-thiazole having a melting point of 83°–84° is obtained.

The starting material can be produced, for example, in the following manner:

4.92 g of ammonium thiocarbamate are suspended in 70 ml of 96% strength ethanol. The suspension is cooled to 5° and, while stirring, 15 g of 2-bromo-1,2-bis-(p-methoxyphenyl)-ethanone are added thereto in portions in the course of 10 minutes, the internal temperature being maintained at approximately 10° by cooling. The mixture is then stirred for 1 hour at 10°, a further 2.4 g of ammonium dithiocarbamate are added and stirring is carried out again for 3 hours at room temperature. The mixture is then poured into 500 ml of ice-water, the crude product is filtered off with suction and then washed with ice-water. For purification, the crude product is suspended in 50 ml of ethanol and heated under reflux, first of all dissolution occurring and, after 90 minutes, reprecipitation. The whole is allowed to cool, filtered with suction and the residue is then washed with cold ethanol. 4,5-bis-(p-methoxyphenyl)-thiazoline-2-thione having a melting point of 226°–230° is obtained.

2-propylthio-4,5-bis-(p-methoxyphenyl)-thiazole, m.p. 58°–60°, can be obtained in an analogous manner.

EXAMPLE 9

In a manner analogous to that described in Example 3, 2-(2-hydroxyethylthio)-4,5-bis-(p-methoxyphenyl)-thiazole, m.p. 82°–84°, is obtained by reacting 4,5-bis-(p-methoxyphenyl)-thiazoline-2-thione with bromoacetic acid methyl ester and subsequent reduction with lithium aluminium hydride.

EXAMPLE 10

0.217 g of ethyl mercaptan is dissolved under nitrogen in 10 ml of hexamethylphosphoric acid triamide, the solution is cooled to 10° and, while stirring, 170 mg of 50% strength sodium hydride suspension (in mineral oil, de-oiled with hexane) are added in portions. The mixture is then stirred for 15 minutes at room temperature, 1.0 g of 2-chloro-4,5-bis-(p-methoxyphenyl)-thiazole is added and stirring is carried out at room temperature for 1 hour. The mixture is then poured into 300 ml of 10% strength sodium chloride solution, digested until crystallisation occurs and filtered with suction and the residue is then washed twice with water and sucked dry on a suction filter. The crude product is recrystallised from methanol. 2-Ethylthio-4,5-bis-(p-methoxyphenyl)-thiazole having a melting point of 73°–75° is obtained.

The 2-chloro-4,5-bis-(p-methoxyphenyl)-thiazole used as starting material may be produced, for example, in the following manner:

100 g of 2-bromo-1,2-bis-(p-methoxyphenyl)-ethanone are mixed with 700 ml of 96% strength ethanol and 25.4 g of sodium thiocyanate and the mixture is heated at 45° for 2 hours. The mixture is then concentrated to dryness by evaporation under reduced pressure, 500 ml of ice-water are added, the mixture is filtered with suction and the residue is then washed twice with ice-water. The crude product is taken up in 1500 ml of methylene chloride, the remaining water is removed and the product is dried over magnesium sulphate. The product is then concentrated to approximately 200 ml, allowed to cool, filtered with suction again, then washed with a little methylene chloride and dried under reduced pressure. 1,2-bis-(p-methoxyphenyl)-2-isothiocyano-ethanone having a melting point of 155° is obtained.

10 g of the 1,2-bis-(p-methoxyphenyl)-2-isothiocyanoethanone so obtained are suspended in 150 ml of diethyl ether and, while stirring, the suspension is cooled to 15°–20°. Gaseous hydrogen chloride is then introduced slowly at such a rate that the reaction temperature does not exceed 20°. After about 45 minutes a clear, yellowish solution is obtained. It is maintained at 15° and a little hydrogen chloride is introduced for a further 7 hours, the solution is left to stand overnight at 15°, poured onto 300 ml of ice, the diethyl ether is removed by distillation, and the crystalline precipitate is filtered with suction, then washed twice with water and sucked dry on a suction filter. The crude product is recrystallised from 100 ml of hexane. 2-Chloro-4,5-bis-(p-methoxyphenyl)-thiazole having a melting point of 92°–94° is obtained.

EXAMPLE 11

2.2 g of 4,5-bis-(p-methoxyphenyl)-thiazole are dissolved in 10 ml of tetrahydrofuran and the solution is cooled to −60°. Then, in the course of 5 minutes, 5 ml of a 1.6 molar solution of butyllithium in hexane are added dropwise thereto, the mixture is subsequently stirred for 10 minutes at −60°, the cooling bath is removed, 1.8 g of dimethyl disulphide dissolved in 20 ml of tetrahydrofuran are slowly added and the mixture is allowed to warm to room temperature while stirring. 50 ml of concentrated ammonium chloride solution are added to the reaction mixture, the organic phase is removed, concentrated to dryness by evaporation, taken up in methylene chloride, washed with water, dried over magnesium sulphate and concentrated to dryness by evaporation again. 2-Methylthio-4,5-bis-(p-methoxyphenyl)-thiazole having a melting point of 102°–104° is obtained.

The starting material can be produced, for example, in the following manner:

7 g of phosphorus pentasulphide in 20 ml of formamide are added to a solution of 7 g of 2-bromo-1,2-bis-(p-methoxyphenyl)-ethanone in 20 ml of benzene and the mixture is heated at the boil for 1 hour. It is allowed to cool, neutralised with 10% strength sodium hydroxide solution and extracted by shaking with chloroform. The organic phase is removed, washed with water, dried over magnesium sulphate and concentrated by evaporation. 4,5-bis-(p-methoxyphenyl)-thiazole having a melting point of 98°–99° is obtained, which can be used without further purification.

EXAMPLE 12

100 g of 4,3-bis-(p-methoxyphenyl)-thiazoline-2-thione are dissolved in 320 ml of 2 N sodium hydroxide solution while stirring. 45 ml of 2-bromoethanol are then added, the mixture is stirred at room temperature for 15 minutes, 500 ml of methylene chloride are added, the mixture is filtered through diatomaceous earth, the organic layer is removed and extracted by washing with 200 ml of 2 N sodium hydroxide solution. The combined aqueous phases are subsequently extracted twice with methylene chloride. The organic phases are combined, dried over magnesium sulphate and concentrated by evaporation under reduced pressure. The remaining oil is dissolved in 700 ml of hot diethyl ether, stirred for 1 hour and caused to crystallise at 10°. The crystals are filtered with suction, then washed twice with 150 ml of ice-cold diethyl ether each time and dried under reduced pressure. 2-(2-Hydroxyethylthio)-4,5-bis-(p-methoxyphenyl)-thiazole having a melting point of 82°–83° is obtained.

EXAMPLE 13

5.0 g of 4,5-bis-(p-methoxyphenyl)-thiazoline-2-thione are dissolved in 30 ml of 2 N sodium hydroxide solution, and 50 g of ice and 100 ml of methylene chloride are added. 2.65 g of bromine dissolved in 5 ml of methylene chloride are added to the vigorously stirred solution and stirring is then continued for 5 minutes. The organic layer is removed and washed with 100 ml of water. The combined aqueous phases are extracted by washing twice with 50 ml of methylene chloride each time. The organic phases are combined, dried over magnesium sulphate and concentrated by evaporation under reduced pressure. The remaining oil is crystallised from diethyl ether, filtered with suction, subsequently washed with diethyl ether, dried under reduced pressure and recrystallised from diethyl ether. 2,2-bis-[4,5-bis-(p-methoxyphenyl)-thiazolyl]-disulphide having a melting point of 155°–158° is obtained.

EXAMPLE 14

35 ml of acetic anhydride are added to 5.0 g of 4,5-bis-(p-methoxyphenyl)-thiazol-2-ylthioglycolic acid (m.p. 143°–145°) under nitrogen, and the mixture is slowly heated to reflux. It is boiled for 5 minutes and immediately cooled to 5°. The precipitated crystals are filtered with suction, washed with ether and dried under reduced pressure. 5,6-bis-(p-methoxyphenyl)-thiazolo[2,3-b]thiazolium-3-oxylate of the formula

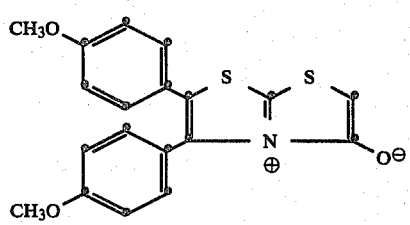

having a melting point of 165°–168° is obtained. In an analogous manner 5,6-bis-phenylthiazolo[2,3-b]thiazolium-3-oxylate is obtained using 4,5-bis-phenylthiazol-2-ylthioglycolic acid as starting material, and 5,6-bis-(p-chlorophenyl)-thiazolo[2,3-b]thiazolium-3-oxylate is obtained using 4,5-bis-(p-chlorophenyl)-thiazol-2-ylthioglycolic acid as starting material.

EXAMPLE 15

0.1 g of 5,6-bis-(p-methoxyphenyl)-thiazolo[2,3-b]thiazolium-3-oxylate are suspended in 5 ml of pyridine and the suspension is heated under reflux for 5 minutes while stirring in a pre-heated oil bath. The suspension is poured into 100 ml of ice-water and digested until the crude product, which separates initially in the form of an oil, crystallises. The crystals are filtered with suction, sucked dry on a suction filter, dissolved in 50 ml of methylene chloride, dried over magnesium sulphate, stirred with 1 g of silica gel, filtered with suction, washed twice with methylene chloride and the combined methylene chloride solutions are concentrated to dryness by evaporation. The crude product is crystallised from 10 ml of methanol. The crystals are filtered with suction and dried under reduced pressure to constant weight. The 1,3-bis-[4,5-bis-(p-methoxyphenyl)-thiazol-2-ylthio]propan-2-one melts at 130°–133°.

EXAMPLE 16

20.0 g of 4,5-bis-(p-methoxyphenyl)-thiazoline-2-thione are dissolved in 100 ml of hexamethylphosphoric acid triamide at 35°. The mixture is allowed to cool to 20°, first 11.2 g of 2-bromoacetaldehyde-dimethylacetal and then, in portions, 2.9 g of 50% strength sodium hydride suspension (in mineral oil, de-oiled with hexane) are added, the reaction temperature being maintained at 25°–30° by cooling. The mixture is then stirred at room temperature for 1 hour, poured onto ice, the oil which separates is brought into solution with diethyl ether, and the organic phase is removed. The aqueous phase is extracted by shaking again with 200 ml of diethyl ether. The organic phases are combined, washed with 200 ml of 2 N sodium hydroxide solution, dried over magnesium sulphate and concentrated by evaporation. The oily crude product is crystallised from hexane and made into a slurry with methanol. 2-[4,5-bis-(p-methoxyphenyl)-thiazol-2-ylthio]-acetaldehyde-dimethylacetal having a melting point of 60°–61° is obtained.

EXAMPLE 17

7.0 g of 2-[4,5-bis-(p-methoxyphenyl)-thiazol-2-ylthio]-acetaldehyde-dimethylacetal are mixed with 50 ml of acetic acid, 25 ml of sulphuric acid and 25 ml of water, stirred vigorously for 30 minutes, and then stirred into 1000 ml of ice-water. The oil which separates is taken up in 200 ml of ethyl acetate. Shaking is carried out with a further 200 ml of ethyl acetate and the combined organic phases are washed with water and then twice with cold sodium bicarbonate solution, dried over magnesium sulphate and concentrated to dryness by evaporation. The crude product is crystallised with diethyl ether. 2-[4,5-bis-(p-methoxyphenyl)-thiazol-2-ylthio]-acetaldehyde having a melting point of 75°–76° is obtained.

EXAMPLE 18

0.10 g of 2-[4,5-bis-(p-methoxyphenyl)-thiazol-2-ylthio]-acetaldehyde is dissolved in 3 ml of methanol, 0.01 g of sodium borohydride is added and the mixture is stirred for 15 minutes. It is then concentrated to dryness by evaporation under reduced pressure and digested with 20 ml of ice-water. After some time crystallisation occurs. After 2 hours the crystals are filtered with suction, washed with water and sucked dry. 2-[2-hydroxyethylthio]-4,5-bis-(p-methoxyphenyl)-thiazole having a melting point of 82°–83° is obtained.

EXAMPLE 19

5.0 g of 4,5-bis-(p-methoxyphenyl)-thiazoline-2-thione are dissolved in 50 ml of hexamethylphosphoric acid triamide under nitrogen at 45°, 0.73 g of 50% strength sodium hydride suspension (in mineral oil, de-oiled with hexane) is added in portions and the mixture is stirred at room temperature for 1 hour. 2.22 g of 3-bromopropanol are then added dropwise. The mixture is then stirred at room temperature for 90 minutes, poured into a mixture of 400 ml of ice-water and 20 ml of 2 N hydrochloric acid, extracted by stirring twice with 100 ml of ethyl acetate each time, washed twice with 100 ml of water each time, dried over sodium sulphate and concentrated by evaporation under reduced pressure. The oily crude product is dissolved in 30 ml of toluene, and chromatographed over a column of 30 g of silica gel with toluene as eluant. The 800–1200 ml fractions are combined, concentrated to dryness by evaporation and dried for 3 hours at 0.01 mbar. Analytically pure 2-(3-hydroxypropylthio)-4,5-bis-(p-methoxyphenyl)-thiazole is obtained in the form of a pale yellow oil, $R_f$ value 0.25 (silica gel thin layer/toluene:ethyl acetate 3:1).

EXAMPLE 20

5.0 g of 2-(2-hydroxyethylthio)-4,5-bis-(p-methoxyphenyl)-thiazole are dissolved in 100 ml of methylene chloride and, while stirring, 2.56 g of m-chloroperbenzoic acid are added in portions. The mixture is then stirred for 15 minutes and subsequently extracted by shaking twice with dilute sodium carbonate solution. The aqueous phase is then washed with methylene chloride. The organic phases are combined, dried over magnesium sulphate and concentrated to dryness by evaporation. The crude product is dissolved in 10 ml of ethyl acetate, precipitated with 30 ml of diethyl ether, filtered with suction, washed with diethyl ether, dried under reduced pressure and, to purify further, made into a slurry with 50 ml of diethyl ether, filtered again and dried at 0.01 mbar and 100° to constant weight. 2-(2-hydroxyethanesulphinyl)-4,5-bis-(p-methoxyphenyl)-thiazole is obtained in the form of a pale yellow oil, $R_f$ value 0.12 (silica gel thin layer/toluene:ethyl acetate 1:1); IR-spectrum: $\nu_{SO} = 1060$ cm$^{-1}$ (3% in CH$_2$Cl$_2$).

EXAMPLE 21

6.0 g of 2-(2-hydroxyethylthio)-4,5-bis-(p-methoxyphenyl)-thiazole are dissolved in 100 ml of methylene chloride and 6.09 g of m-chloroperbenzoic acid are added in portions. The mixture is stirred at room temperature for 10 minutes and then is heated under reflux for 1 hour until potassium iodide paper is no longer coloured. The mixture is allowed to cool, washed with ice-cold N-sodium hydroxide solution, and extracted with methylene chloride, the organic phases are combined, dried over magnesium sulphate and concentrated to dryness by evaporation. The crude product is dissolved in 20 ml of toluene/ethyl acetate and purified by chromatography over 60 g of silica gel. The first 150 ml of eluate are collected, concentrated to dryness by evaporation and dried at 100° and 0.018 mbar to constant weight. Analytically pure 2-(2-hydroxyethanesulphonyl)-4,5-bis-(p-methoxyphenyl)-thiazole is obtained in the form of a pale yellow oil, $R_f$ value 0.21 (silica gel thin layer/toluene:ethyl acetate 3:1); IR-spectrum: $\nu_{SO_2} = 1170$ cm$^{-1}$, 1225 cm$^{-1}$ (3% in CH$_2$Cl$_2$).

EXAMPLE 22

0.23 g of sodium are dissolved in 30 ml of ethanol under nitrogen. The solution is allowed to cool to room temperature, while stirring 3 g of 4,5-bis-(p-methoxyphenyl)-thiazoline-2-thione are added and, once dissolution is complete, ethylene oxide is introduced, the reaction temperature being maintained at 25°–30° by gentle cooling. After introducing the ethylene oxide for 30 minutes, it should not be possible to detect any more thione by thin layer chromatography. 10 ml of 2 N-ammonium chloride are then added, the ethanol is removed by distillation under reduced pressure, and the residue obtained by concentration by evaporation is shaken with a mixture of 50 ml of water and 50 ml of methylene chloride. The organic phase is removed, then shaken with methylene chloride, dried over magnesium sulphate and concentrated to dryness by evaporation. The oily crude product is caused to crystallise by triturating with 20 ml of diethyl ether and dried under reduced pressure. 2-(2-Hydroxyethylthio)-4,5-bis-(p-methoxyphenyl)-thiazole having a melting point of 82°–83° is obtained.

EXAMPLE 23

15.0 g of 4,5-bis-(p-methoxyphenyl)-thiazoline-2-thione are dissolved in 50 ml of 2 N sodium hydroxide solution, 15.4 g of bromoacetaldehyde-dimethylacetal (2,2-dimethoxy-1-bromoethane) are added under nitrogen and the mixture is heated to 80° while stirring. The mixture is stirred at 80° for 2.5 hours, cooled to room temperature, extracted by shaking with 100 ml of toluene, the organic layer is removed and the aqueous phase is subsequently shaken with 50 ml of toluene. The organic phases are combined, washed twice with 30 ml of 2 N sodium hydroxide solution each time and then with 30 ml of 2 N hydrochloric acid, dried over magnesium sulphate, concentrated by evaporation under reduced pressure and carefully dried. The crude product is crystallised from hexane/methanol (50 ml + 5 ml). 2-[4,5-bis-(p-methoxyphenyl)-thiazol-2-ylthio]-acetaldehyde-dimethylacetal having a melting point of 60°–61° is obtained.

EXAMPLE 24

7.0 g of 2-[4,5-bis-(p-methoxyphenyl)-thiazol-2-ylthio]-acetaldehyde-dimethylacetal are dissolved in 200 ml of methylene chloride, the solution is cooled to 5°, 3.53 g of m-chloroperbenzoic acid (90% strength) are added and the mixture is stirred for 15 minutes at 5°. 100 g of ice and 50 ml of 2 N sodium hydroxide solution are added, the organic phase is removed and then washed with 50 ml of 2 N sodium hydroxide solution, and the aqueous phase is extracted by stirring twice with 50 ml of methylene chloride each time. The organic phases are combined, dried over magnesium sulphate and concentrated to dryness by evaporation. The crude product is purified by chromatography over 110 g of silica gel, and with toluene/ethyl acetate (9:1) 2-[4,5-bis-o-methoxyphenyl)-thiazol-2-ylsulphonyl]-acetaldehyde-dimethylacetal, and with toluene/ethyl acetate (1:1) 2-[4,5-bis-(p-methoxyphenyl)-thiazol-2-ylsulphinyl]-acetaldehyde-dimethylacetal, are eluted as oils.

EXAMPLE 25

5.75 g of 2-[4,5-bis-(p-methoxyphenyl)-thiazol-2-ylsulphinyl]-acetaldehyde-dimethylacetal are dissolved in 5 ml of acetic acid. Then, while stirring, 30 ml of a mixture of 2 parts acetic acid, 1 part sulphuric acid and 1 part water are added dropwise over a period of 5 minutes. The mixture is stirred at room temperature for 30 minutes, diluted with 100 ml of methylene chloride and poured into 200 ml of ice-water. The organic layer is removed and washed with 200 ml of ice-water. The aqueous phase is extracted by shaking three times with 50 ml of methylene chloride each time. The organic phases are combined, dried over magnesium sulphate and concentrated to dryness by evaporation. The crude product is dissolved in 200 ml of methylene chloride and stirred with 5 g of silica gel. The mixture is filtered, concentrated to dryness by evaporation and dried under reduced pressure. 2-[4,5-bis-(p-methoxyphenyl)-thiazol-2-ylsulphinyl]-acetaldehyde is obtained in the form of a highly viscous oil, IR-spectrum: $\nu_{C=O} = 1720$ cm$^{-1}$, $\nu_{S=O} = 1080$ cm$^{-1}$(CCl$_4$).

EXAMPLE 26

8.0 g of 2-[4,5-bis-(p-methoxyphenyl)-thiazol-2-ylthio]-acetaldehyde-dimethylacetal are dissolved in 200 ml of methylene chloride, 8.08 g of m-chloroperbenzoic acid are added in portions and the mixture is stirred at room temperature for 2 hours. The mixture is then extracted by shaking twice with 100 ml of cold N sodium hydroxide solution each time, the aqueous extracts are washed twice with 50 ml of methylene chloride each time, and the organic phases are combined, dried over magnesium sulphate and concentrated to dryness by evaporation. The residue obtained by concentration by evaporation is dissolved in 200 ml of toluene/ethyl acetate (10:1), stirred with 10 g of silica gel, filtered and concentrated by evaporation again. 2-[4,5-bis-(p-methoxyphenyl)-thiazol-2-ylsulphonyl]-acetaldehyde-dimethylacetal is obtained in the form of a yellowish oil.

EXAMPLE 27

7.15 g of 2-[4,5-bis-(p-methoxyphenyl)-thiazol-2-ylsulphonyl]-acetaldehyde-dimethylacetal are hydrolysed in the manner described in Example 25 to 2-[4,5-bis-(p-methoxyphenyl)-thiazol-2-ylsulphonyl]-acetaldehyde (highly viscous oil), IR-spectrum: $\nu_{C=O}=1720$ cm$^{-1}$, $\nu_{S=O}=1145$ cm$^{-1}+1325$ cm$^{-1}$ (CCl$_4$).

EXAMPLE 28

4.0 g of 2-[4,5-bis-(p-methoxyphenyl)-thiazol-2-ylthio]-2-formylacetic acid ethyl ester are dissolved in 50 ml of acetic acid, 10 ml of 43% strength hydrobromic acid are added and the mixture is heated at 80° for 4 hours. The mixture is concentrated to dryness by evaporation under reduced pressure, and the residue is dissolved in 200 ml of ethyl acetate, washed twice with 50 ml of saturated sodium bicarbonate solution each time and with water, dried over magnesium sulphate and concentrated to dryness by evaporation. The crude product is recrystallised from hexane/diethyl ether (55 ml+10 ml). 2-[4,5-bis-(p-methoxyphenyl)-thiazol-2-ylthio]-acetaldehyde having a melting point of 75°–76° is obtained.

The starting material can be produced, for example, in the following manner:

3.3 g of 4,5-bis-(p-methoxyphenyl)-thiazoline-2-thione are dissolved in 50 ml of hexamethylphosphoric acid triamide, the solution is cooled to 5° and converted into the sodium salt under nitrogen with sodium hydride (0.5 g of a 50% strength suspension in mineral oil, de-oiled with hexane). The product is allowed to warm to room temperature, 2.0 g of 2-bromoformylacetic acid ethyl ester are added dropwise and the mixture is stirred at 25° for 1 hour, poured into 750 ml of ice-water and taken up in diethyl ether. The ethereal phase is washed with water, dried over magnesium sulphate and concentrated to dryness by evaporation. 2-[4,5-bis-(p-methoxyphenyl)-thiazol-2-ylthio]-2-formylacetic acid ethyl ester is obtained, which can be used without further purification.

EXAMPLE 29

1.49 g of potassium pyrosulphite are dissolved in 5 ml of water. A solution of 2.5 g of 2-[4,5-bis-(p-methoxyphenyl)-thiazol-2-ylthio]-acetaldehyde in 40 ml of ethanol is then added and the mixture is stirred for 30 minutes at room temperature and for 15 minutes at 5°–10°, filtered with suction, washed twice with cold ethanol and twice with diethyl ether and dried under reduced pressure. The potassium salt of 2-[4,5-bis-(p-methoxyphenyl)-thiazol-2-ylthio]-1-hydroxyethanesulphonic acid is obtained. It melts at 165° (decomposition).

EXAMPLE 30

3.28 g of 2,2-bis-[4,5-bis-(p-methoxyphenyl)-thiazolyl]-disulphide in 50 ml of tetrahydrofuran are added dropwise to a propylmagnesium bromide solution (prepared from 0.24 g of magnesium activated with iodine and 0.9 ml of propylbromide in 10 ml of tetrahydrofuran). The mixture is heated under reflux for 90 minutes, allowed to cool, 100 ml of saturated ammonium chloride solution are added dropwise and the mixture is extracted by shaking three times with 100 ml of diethyl ether each time. The ethereal solutions are combined, washed three times with 100 ml of water each time, dried over magnesium sulphate and concentrated to dryness by evaporation. The crude product is purified over 15 g of silica gel using toluene/ethyl acetate (10:1) as eluant and recrystallised from methanol. 2-Propylthio-4,5-bis-(p-methoxyphenyl)-thiazole having a melting point of 58°–60° is obtained.

EXAMPLE 31

5.0 g of 2-(2-hydroxyethylthio)-4,5-bis-(p-methoxyphenyl)-thiazole are suspended in 50 ml of acetic anhydride and, while stirring, the suspension is heated to the boil and refluxed for 15 minutes. The product is concentrated to dryness by evaporation under reduced pressure, two 30 ml portions of xylene are added, with concentration by evaporation being carried out again after each addition to remove traces of acetic anhydride, and the residue is dried under reduced pressure. 2-(2-Acetoxyethylthio)-4,5-bis-(p-methoxyphenyl)-thiazole is obtained in the form of an oil, $R_f=0.33$ (silica gel toluene/ethyl acetate 10:1), IR-spectrum: $\nu_{C=O}=1730$ cm$^{-1}$ (CCl$_4$).

EXAMPLE 32

0.5 g of 4,5-bis-(p-methoxyphenyl)-thiazoline-2-thione are dissolved in 2.6 ml of 2 N sodium hydroxide solution while stirring. 0.367 g of allyl bromide is added, the mixture is stirred at room temperature for 10 minutes, extracted by shaking twice with 10 ml of toluene each time, the combined aqueous phases are washed twice with 5 ml of 2 N sodium hydroxide solution each time, dried over magnesium sulphate, concentrated by evaporation under reduced pressure and crystallised from hexane. 2-Allylthio-4,5-bis-(p-methoxyphenyl)-thiazole having a melting point of 57°–58° is obtained.

EXAMPLE 33

0.2 g of 2-[4,5-bis-(p-methoxyphenyl)-thiazol-2-ylthio]acetaldehyde are dissolved in 50 ml of toluene. While stirring vigorously, 1 ml of ethylene glycol and then 0.2 g of p-toluenesulphonic acid are added. The mixture is heated for 40 hours in a water separator, cooled to 20°, filtered with suction, crystallised from hexane/benzene and dried under reduced pressure to constant weight. 2-[4,5-bis-(p-methoxyphenyl)-thiazol-2-ylthio]acetaldehyde-ethyleneacetal is obtained in the form of a viscous oil.

EXAMPLE 34

Analogously to Examples 1–33, or as described in the description, it is furthermore possible to produce the following:

2-(1,1,2,2-tetrafluoroethylthio)-4,5-bis-phenylthiazole,
2-(1,1,2,2-tetrafluoroethylthio)-4,5-bis-(p-chlorophenyl)-thiazole,
2-(1,1,2,2-tetrafluoroethylthio)-4,5-bis-(p-methoxyphenyl)-thiazole,
2-(3-hydroxypropanesulphinyl)-4,5-bis-(p-methoxyphenyl)-thiazole,
2-(3-hydroxypropanesulphonyl)-4,5-bis-(p-methoxyphenyl)-thiazole,
2-(2-hydroxyethanesulphonyl)-4,5-phenylthiazole,
2-(2-hydroxyethanesulphonyl)-4,5-bis-(p-chlorophenyl)-thiazole, 2-methanesulphonyl-4,5-bis-(p-methoxyphenyl)-thiazole,
2-ethanesulphonyl-4,5-bis-(p-methoxyphenyl)-thiazole,
2-(2-hydroxyethylthio)-4-(p-methoxyphenyl)-5-(4-pyridyl)-thiazole,
2-(2-hydroxyethylthio)-4-phenyl-5-(3-pyridyl)-thiazole,
2-(2-hydroxyethanesulphonyl)-4,5-bis-(p-methoxyphenyl)-thiazole,
2-propargylthio-4,5-bis-(p-methoxyphenyl)-thiazole,
2-ethynylthio-4,5-bis-(p-methoxyphenyl)-thiazole,
2-(2-methoxyethylthio)-4,5-bis-(p-methoxyphenyl)-thiazole,
2-(2-methylthioethylthio)-4,5-bis-(p-methoxyphenyl)-thiazole,
3-[4,5-bis-(p-methoxyphenyl)-thiazol-2-ylthio]-propionaldehyde,
3-[4,5-bis-(p-methoxyphenyl)-thiazol-2-ylthio]-propionaldehyde-dimethylacetal,
2-(2,3-dimethoxypropylthio)-4,5-bis-(p-methoxyphenyl)-thiazole,
2-(2,3-dihydroxypropylthio)-4,5-bis-(p-methoxyphenyl)-thiazole,
2-(2,3-isopropylidenedioxypropylthio)-4,5-bis-(p-methoxyphenyl)-thiazole,
2-(2,2-ethylenedithioethylthio)-4,5-bis-(p-methoxyphenyl)-thiazole,
2-(2-hydroxyethanesulphinyl)-5-phenyl-4-(3-pyridyl)-thiazole,
2-(2-hydroxyethanesulphonyl)-5-phenyl-4-(3-pyridyl)-thiazole,
2-methanesulphinyl-5-phenyl-4-(3-pyridyl)-thiazole,
2-methanesulphonyl-5-phenyl-4-(3-pyridyl)-thiazole,
2-ethanesulphinyl-5-phenyl-4-(3-pyridyl)-thiazole,
2-ethanesulphonyl-5-phenyl-4-(3-pyridyl)-thiazole,
2-(2-hydroxyethanesulphinyl)-5-phenyl-4-(3-pyridyl)-thiazole,
2-(2-hydroxyethanesulphonyl)-5-phenyl-4-(3-pyridyl)-thiazole,
2-(1,1,2,2-tetrafluoroethylthio)-5-phenyl-4-(2-pyridyl)-thiazole,
2-methylthio-4-phenyl-5-(3-pyridyl)-thiazole,
2-ethylthio-4-phenyl-5-(3-pyridyl)-thiazole,
1,3-bis-[5-phenyl-4-(3-pyridyl)-thiazol-2-ylthio]-propan-2-ol,
1,3-bis-[5-phenyl-4-(3-pyridyl)-thiazol-2-ylthio]-propan-2-one,
2,2'-bis-[5-phenyl-4-(3-pyridyl)-thiazolyl]-disulphide,
2-(2-hydroxyethylthio)-4-phenyl-5-(2-thienyl)-thiazole,
2-methanesulphinyl-4-phenyl-5-(3-pyridyl)-thiazole,
2-methanesulphonyl-4-phenyl-5-(3-pyridyl)-thiazole,
2-ethanesulphonyl-4-phenyl-5-(3-pyridyl)-thiazole,
2-ethanesulphinyl-4-phenyl-5-(3-pyridyl)-thiazole,
2-(2-hydroxyethanesulphinyl)-4-phenyl-5-(3-pyridyl)-thiazole, and
2-(2-hydroxyethanesulphonyl)-4-phenyl-5-(3-pyridyl)-thiazole.

EXAMPLE 35

1.2 g of 2-(2-bromoethylthio)-4,5-bis-(p-methoxyphenyl)-thiazole are dissolved in 10 ml of polyethylene glycol, 0.5 ml of water and 0.5 g of potassium hydroxide are added, the mixture is heated at 120° for 30 minutes, cooled to room temperature, diluted with 50 ml of water and left to stand at +5° for 2 hours. The precipitated crystals are filtered off and recrystallised from diethyl ether/hexane. 2-(2-Hydroxyethylthio)-4,5-bis-(p-methoxyphenyl)-thiazole having a melting point of 82°–83° is obtained.

The starting material can be obtained, for example, in the following manner:

2.0 g of 4,5-bis-(p-methoxyphenyl)-thiazoline-2-thione are dissolved in 10.4 ml of 2 N sodium hydroxide solution. 2.3 g of dibromoethane are added and the mixture is stirred at room temperature for 4 hours. The organic layer is then removed, the aqueous phase is subsequently shaken with 10 ml of toluene, and the combined organic phases are washed twice with 5 ml of 2 N sodium hydroxide solution each time, dried over magnesium sulphate and concentrated to dryness by evaporation under reduced pressure. 2-(2-Bromoethylthio)-4,5-bis-(p-methoxyphenyl)-thiazole, $R_f=0.65$ (silica gel, toluene/ethyl acetate 10:1) is obtained.

EXAMPLE 36

0.8 g of 2-(2-bromoethylthio)-4,5-bis-(p-methoxyphenyl)-thiazole are dissolved in 20 ml of toluene. 2 ml of a 30% strength solution of tetrabutylammonium hydroxide in water are added and the mixture is heated under reflux for 2 hours while stirring vigorously. The mixture is then allowed to cool, the organic phase is separated off, washed twice with 10 ml of water each time, dried over sodium sulphate and concentrated to dryness by evaporation. The crude product is purified by chromatography over a silica gel column with toluene/ethyl acetate (10:1) as eluant. The fractions that according to the thin layer chromatogram contain 2-vinylthio-4,5-bis-(p-methoxyphenyl)-thiazole are concentrated by evaporation and dried to constant weight. 2-Vinylthio-4,5-bis-(p-methoxyphenyl)-thiazole is obtained in the form of a pale yellow oil.

EXAMPLE 37

Tablets containing 25 mg of active ingredient, for example 2-(2-hydroxyethylthio)-4,5-bis-(p-methoxyphenyl)-thiazole, can be produced as follows:

Ingredients (for 1000 tablets)

active ingredient: 25.0 g
lactose: 100.7 g
wheat starch: 7.5 g
polyethylene glycol 6000: 5.0 g
talc: 5.0 g
magnesium stearate: 1.8 g
demineralised water: q.s.

Manufacture

All of the solid ingredients are first of all forced through a sieve having a mesh width of 0.6 mm. Then, the active ingredient, the lactose, the talc, the magnesium stearate and half the starch are mixed. The other half of the starch is suspended in 40 ml of water and this suspension is added to a boiling solution of the polyethylene glycol in 100 ml of water and the mixture is granulated, if necessary with the addition of water. The granules are dried overnight at 35°, forced through a sieve having a mesh width of 1.2 mm and pressed to form tablets approximately 6 mm in diameter that are concave on both sides.

EXAMPLE 38

Tablets containing 10 mg of active ingredient, for example 2-(2-hydroxyethylthio)-4,5-bis-(p-methoxyphenyl)-thiazole, can be produced as follows:

Ingredients (for 1000 tablets)

active ingredient: 10.0 g lactose: 100.7 g
wheat starch: 7.5 g
polyethylene glycol 6000: 5.0 g
talc: 5.0 g
magnesium stearate: 1.8 g
demineralised water: q.s.

Manufacture

All of the solid ingredients are first of all forced through a sieve having a mesh width of 0.6 mm. Then, the active ingredient, the lactose, the talc, the magnesium stearate and half the starch are mixed. The other half of the starch is suspended in 40 ml of water and this suspension is added to a boiling solution of the polyethylene glycol in 100 ml of water and the mixture is granulated, if necessary with the addition of water. The granules are dried overnight at 35°, forced through a sieve having a mesh width of 1.2 mm and pressed to form tablets approximately 6 mm in diameter that are concave on both sides.

EXAMPLE 39

Tablets containing 75 mg of active ingredient, for example 2-(2-hydroxyethylthio)-4,5-bis-(p-methoxyphenyl)-thiazole, can be produced as follows:

Ingredients (for 1000 tablets)

active ingredient: 75.0 g
lactose: 100.7 g
wheat starch: 7.5 g
polyethylene glycol 6000: 5.0 g
talc: 5.0 g
magnesium stearate: 1.8 g
demineralised water: q.s.

Manufacture

All of the solid ingredients are first of all forced through a sieve having a mesh width of 0.6 mm. Then, the active ingredient, the lactose, the talc, the magnesium stearate and half the starch are mixed. The other half of the starch is suspended in 40 ml of water and this suspension is added to a boiling solution of the polyethylene glycol in 100 ml of water and the mixture is granulated, if necessary with the addition of water. The granules are dried overnight at 35°, forced through a sieve having a mesh width of 1.2 mm and pressed to form tablets approximately 6 mm in diameter that are concave on both sides.

EXAMPLE 40

Analogously to Examples 37–39, it is also possible to produce tablets containing another compound from the compounds obtainable according to Examples 1–36.

We claim:

1. A novel 2,4,5-trisubstituted thiazole of the formula

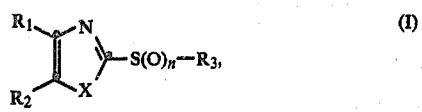

in which at least one of the radicals $R_1$ and $R_2$ represents optionally N-oxidised pyridyl and the other represents phenyl which is unsubstituted or substituted by lower alkyl, lower alkoxy, hydroxy, halogen or lower alkanoyloxy, lower alkylthio, lower alkanesulphinyl, lower alkanesulphonyl, amino, mono- or di-lower alkylamino, nitro and/or by trifluoromethyl, X represents thio, n represents 0, 1 or 2, $R_3$ represents lower alkyl, lower alkenyl or lower alkynyl, mono- or di-lower alkoxy-lower alkyl, lower alkylenedioxy-lower alkyl, lower alkanoyloxy-lower alkyl carrying the lower alkanoyloxy group in a position higher than the α-position, polyhalo-lower alkyl, hydroxy-lower alkyl wherein the hydroxy group is at a position higher than the α-position, oxo-lower alkyl carrying the oxo group in a position higher than the α-position, or phenyl-lower alkyl that is unsubstituted or substituted as indicated for $R_1$ and $R_2$, or a pharmaceutically acceptable salt thereof.

2. A compound according to claim 1 of the formula I in which at least one of $R_1$ and $R_2$ represents unsubstituted optionally N-oxidised pyridyl and the other denotes phenyl that is unsubstituted or substituted by lower alkoxy, hydroxy, halogen, lower alkanoyloxy, lower alkylthio, lower alkanesulphinyl, di-lower alkylamino and/or trifluoromethyl, X represents thio, n represents 0, 1 or 2, $R_3$ represents lower alkyl, or lower alkenyl or lower alkynyl each of which is bonded via a saturated carbon atom, lower alkoxy-lower alkyl, lower alkanoyloxy-lower alkyl carrying the lower alkanoyloxy group in a position higher than the α-position, lower hydroxy-lower alkyl which carries the hydroxy group in a position higher than the α-position, or oxo-lower alkyl carrying the oxo group in a position higher than the α-position, or a pharmaceutically acceptable salt thereof.

3. A compound according to claim 1 of the formula I in which at least one of the radicals $R_1$ and $R_2$ represents optionally N-oxidised pyridyl, and the other represents phenyl that is unsubstituted or substituted by lower alkoxy having up to and including 4 carbon atoms, lower alkylthio having up to and including 4 carbon atoms, halogen having an atomic number of up to and including 35, hydroxy and/or trifluoromethyl, X represents thio, n represents 0, 1 or 2, and $R_3$ represents lower alkyl having up to and including 4 carbon atoms, or any one of the following, each of which carries the oxo, hydroxy, lower alkanoyloxy, lower alkoxy or lower alkylenedioxy group(s) in a position higher than the α-position: oxo- or hydroxy-lower alkyl each having up to and including 4 carbon atoms, lower alkanoyloxy-lower alkyl, each moiety having up to and including 4 carbon atoms, mono- or di-lower alkoxy-lower alkyl, each moiety having up to and including 4 carbon atoms, or lower alkylenedioxy-lower alkyl, each moiety having up to and including 4 carbon atoms, or a pharmaceutically acceptable salt thereof.

4. A compound according to claim 1 of the formula I in which at least one of the radicals $R_1$ and $R_2$ represents pyridyl and the other represents phenyl that is unsubstituted or substituted by lower alkoxy having up to and including 4 carbon atoms or halogen having an atomic number of up to and including 35, X represents thio, n represents 0, 1 or 2, and $R_3$ represents lower alkyl having up to and including 4 carbon atoms, ω-hydroxy-lower alkyl having from 2 to 4 carbon atoms, or 2- or 3-lower alkoxy-lower alkyl having up to and including 4 carbon atoms, or a pharmaceutically acceptable salt thereof.

5. A compound according to claim 1 that is 2-methylthio-5-phenyl-4-(3-pyridyl)-thiazole or a pharmaceutically acceptable salt thereof.

6. A compound according to claim 1 that is 2-ethylthio-5-phenyl-4-(3-pyridyl)-thiazole or a pharmaceutically acceptable salt thereof.

7. A compound according to claim 1 that is 2-(2-hydroxyethylthio)-5-phenyl-4-(3-pyridyl)-thiazole or a pharmaceutically acceptable salt thereof.

8. A compound according to claim 1 that is 2-methanesulphinyl-5-phenyl-4-(3-pyridyl)-thiazole or a pharmaceutically acceptable salt thereof.

9. A compound according to claim 1 that is 2-methanesulphonyl-5-phenyl-4-(3-pyridyl)-thiazole or a pharmaceutically acceptable salt thereof.

10. A compound according to claim 1 that is 2-ethanesulphinyl-5-phenyl-4-(3-pyridyl)-thiazole or a pharmaceutically acceptable salt thereof.

11. A compound according to claim 1 that is 2-ethanesulphonyl-5-phenyl-4-(3-pyridyl)-thiazole or a pharmaceutically acceptable salt thereof.

12. A compound according to claim 1 that is 2-(2-hydroxyethanesulphinyl)-5-phenyl-4-(3-pyridyl)-thiazole or a pharmaceutically acceptable salt thereof.

13. A compound according to claim 1 that is 2-(2-hydroxyethanesulphonyl)-5-phenyl-4-(3-pyridyl)-thiazole or a pharmaceutically acceptable salt thereof.

14. A compound according to claim 1 that is 2-(1,1,2,2-tetrafluoroethylthio)-5-phenyl-4-(3-pyridyl)-thiazole or a pharmaceutically acceptable salt thereof.

15. A compound according to claim 1 that is 2-methylthio-4-phenyl-5-(3-pyridyl)-thiazole or a pharmaceutically acceptable salt thereof.

16. A compound according to claim 1 that is 2-ethylthio-4-phenyl-5-(3-pyridyl)-thiazole or a pharmaceutically acceptable salt thereof.

17. A compound according to claim 1 that is 2-(2-hydroxyethylthio)-4-phenyl-5-(3-pyridyl)-thiazole or a pharmaceutically acceptable salt thereof.

18. A compound according to claim 1 that is 2-methanesulphinyl-4-phenyl-5-(3-pyridyl)-thiazole or a pharmaceutically acceptable salt thereof.

19. A compound according to claim 1 that is 2-methanesulphonyl-4-phenyl-5-(3-pyridyl)-thiazole or a pharmaceutically acceptable salt thereof.

20. A compound according to claim 1 that is 2-ethanesulphonyl-4-phenyl-5-(3-pyridyl)-thiazole or a salt thereof.

21. A compound according to claim 1 that is 2-ethanesulphinyl-4-phenyl-5-(3-pyridyl)-thiazole or a pharmaceutically acceptable salt thereof.

22. A compound according to claim 1 that is 2-(2-hydroxyethanesulphinyl)-4-phenyl-5-(3-pyridyl)-thiazole or a pharmaceutically acceptable salt thereof.

23. A compound according to claim 1 that is 2-(2-hydroxyethanesulphonyl)-4-phenyl-5-(3-pyridyl)-thiazole or a pharmaceutically acceptable salt thereof.

24. A compound according to claim 1 that is 2-(2-hydroxyethylthio)-4-phenyl-5-(3-pyridyl)-thiazole or a pharmaceutically acceptable salt thereof.

25. An antiinflammatory pharmaceutical composition comprising an effective amount of a compound according to claim 1 in the presence of a pharmaceutically acceptable carrier.

26. A method for treating inflammation comprising administering to warm blooded animals in need of such administration an effective amount of a compound according to claim 1.

* * * * *